United States Patent
Harris et al.

(10) Patent No.: US 10,806,451 B2
(45) Date of Patent: Oct. 20, 2020

(54) SURGICAL STAPLER WITH COOPERATING DISTAL TIP FEATURES ON ANVIL AND STAPLE CARTRIDGE

(71) Applicant: ETHICON LLC, Guaynabo, PR (US)

(72) Inventors: Jason L. Harris, Lebanon, OH (US); Gregory J. Bakos, Mason, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 395 days.

(21) Appl. No.: 15/435,618

(22) Filed: Feb. 17, 2017

(65) Prior Publication Data

US 2018/0235611 A1    Aug. 23, 2018

(51) Int. Cl.
*A61B 17/072* (2006.01)
*A61B 17/00* (2006.01)

(52) U.S. Cl.
CPC ...... *A61B 17/072* (2013.01); *A61B 17/07207* (2013.01); *A61B 2017/0053* (2013.01); *A61B 2017/00477* (2013.01); *A61B 2017/00738* (2013.01); *A61B 2017/00862* (2013.01); *A61B 2017/07242* (2013.01); *A61B 2017/07257* (2013.01); *A61B 2017/07271* (2013.01)

(58) Field of Classification Search
CPC ............... A61B 17/064; A61B 17/068; A61B 17/07929; A61B 2017/0053; A61B 2017/07271; A61B 2017/07257; A61B 2017/00738; A61B 2017/07292
USPC .......................................... 227/175.1–182.1
See application file for complete search history.

(56) References Cited

U.S. PATENT DOCUMENTS

| | | | |
|---|---|---|---|
| 4,805,823 | A | 2/1989 | Rothfuss |
| 5,415,334 | A | 5/1995 | Williamson et al. |
| 5,465,895 | A | 11/1995 | Knodel et al. |
| 5,597,107 | A | 1/1997 | Knodel et al. |

(Continued)

FOREIGN PATENT DOCUMENTS

| | | |
|---|---|---|
| EP | 1 617 768 | 1/2006 |
| EP | 2 674 111 A2 | 12/2013 |

(Continued)

OTHER PUBLICATIONS

U.S. Appl. No. 15/435,573, filed Feb. 17, 2017.

(Continued)

*Primary Examiner* — Chelsea E Stinson
*Assistant Examiner* — Himchan "Aiden" Song
(74) *Attorney, Agent, or Firm* — Frost Brown Todd LLC

(57) ABSTRACT

A surgical instrument includes a body portion, a shaft, and an end effector that is operable to compress, staple, and cut tissue. The end effector includes and anvil and a staple cartridge. The anvil has a body and a modular releasable curved tip that connects with the body. The curved tip may be elastically deformable. The curved anvil tip and the tip of the cartridge include cooperating features that assist in gripping tissue during clamping. A separate cartridge may be provided that retains a replacement anvil tip and a replacement staple cartridge, where the replacement anvil tip and staple cartridge include the cooperating features. The separate cartridge may also include anvil tip and staple cartridge removal features to assist in removal of previously installed anvil tips and staple cartridges.

20 Claims, 18 Drawing Sheets

(56) References Cited

U.S. PATENT DOCUMENTS

| | | |
|---|---|---|
| 5,632,432 A | 5/1997 | Schulze et al. |
| 5,673,840 A | 10/1997 | Schulze et al. |
| 5,704,534 A | 1/1998 | Huitema et al. |
| 5,792,135 A | 8/1998 | Madhani et al. |
| 5,814,055 A | 9/1998 | Knodel et al. |
| 5,817,084 A | 10/1998 | Jensen |
| 5,878,193 A | 3/1999 | Wang et al. |
| 6,231,565 B1 | 5/2001 | Tovey et al. |
| 6,364,888 B1 | 4/2002 | Niemeyer et al. |
| 6,783,524 B2 * | 8/2004 | Anderson ............... A61B 34/70 606/28 |
| 6,978,921 B2 | 12/2005 | Shelton et al. |
| 7,000,818 B2 | 2/2006 | Shelton et al. |
| 7,143,923 B2 | 12/2006 | Shelton et al. |
| 7,303,108 B2 | 12/2007 | Shelton |
| 7,367,485 B2 | 5/2008 | Shelton et al. |
| 7,380,695 B2 | 6/2008 | Doll et al. |
| 7,380,696 B2 | 6/2008 | Shelton et al. |
| 7,404,508 B2 | 7/2008 | Smith et al. |
| 7,434,715 B2 | 10/2008 | Shelton et al. |
| 7,524,320 B2 | 4/2009 | Tierney et al. |
| 7,644,848 B2 | 1/2010 | Swayze et al. |
| 7,691,098 B2 | 4/2010 | Wallace et al. |
| 7,721,930 B2 | 5/2010 | McKenna et al. |
| 7,806,891 B2 | 10/2010 | Nowlin et al. |
| 8,136,711 B2 * | 3/2012 | Beardsley ........ A61B 17/07207 227/175.1 |
| 8,210,411 B2 | 7/2012 | Yates et al. |
| 8,408,439 B2 | 4/2013 | Huang et al. |
| 8,449,560 B2 | 5/2013 | Roth et al. |
| 8,453,914 B2 | 6/2013 | Laurent et al. |
| 8,479,969 B2 | 7/2013 | Shelton |
| 8,573,461 B2 | 11/2013 | Shelton et al. |
| 8,573,465 B2 | 11/2013 | Shelton |
| 8,602,288 B2 | 12/2013 | Shelton et al. |
| 8,616,431 B2 | 12/2013 | Timm et al. |
| 8,783,541 B2 | 7/2014 | Shelton et al. |
| 8,800,838 B2 | 8/2014 | Shelton |
| 8,820,605 B2 | 9/2014 | Shelton |
| 8,844,789 B2 | 9/2014 | Shelton et al. |
| 9,011,434 B2 | 4/2015 | Kappel et al. |
| 9,186,142 B2 | 11/2015 | Fanelli et al. |
| 9,198,662 B2 | 12/2015 | Barton et al. |
| 9,301,753 B2 | 4/2016 | Aldridge et al. |
| 9,301,759 B2 | 4/2016 | Spivey et al. |
| 9,333,003 B2 * | 5/2016 | Kappel .................. A61B 17/29 |
| 9,517,065 B2 | 12/2016 | Simms et al. |
| D833,010 S | 11/2018 | Harris et al. |
| 2004/0243151 A1 * | 12/2004 | Demmy ............... A61B 17/105 606/139 |
| 2005/0139633 A1 * | 6/2005 | Wukusick ............ A61B 17/072 227/176.1 |
| 2012/0241491 A1 * | 9/2012 | Aldridge ......... A61B 17/07292 227/175.1 |
| 2013/0146643 A1 * | 6/2013 | Schmid .............. A61B 17/0643 227/180.1 |
| 2013/0334280 A1 * | 12/2013 | Krehel ............. A61B 17/07207 227/176.1 |
| 2014/0097227 A1 * | 4/2014 | Aronhalt ............ A61B 17/0644 227/180.1 |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239041 A1 | 8/2014 | Zerkle |
| 2014/0239043 A1 * | 8/2014 | Simms ............. A61B 17/07207 227/176.1 |
| 2014/0239044 A1 | 8/2014 | Hoffman |
| 2015/0083776 A1 * | 3/2015 | Lim ................. A61B 17/07207 227/175.1 |
| 2015/0272575 A1 | 10/2015 | Leimbach et al. |
| 2016/0120544 A1 * | 5/2016 | Shelton, IV ...... A61B 17/07207 227/177.1 |
| 2018/0021051 A1 * | 1/2018 | Worrell .................. A61B 17/29 227/175.1 |

FOREIGN PATENT DOCUMENTS

| | | | |
|---|---|---|---|
| EP | 2 772 202 A2 | 9/2014 | |
| EP | 2 772 203 A2 | 9/2014 | |
| EP | 2 777 523 A1 | 9/2014 | |
| EP | 2913010 A2 * | 9/2015 | ....... A61B 17/07207 |
| WO | WO 2004/096057 A2 | 11/2004 | |

OTHER PUBLICATIONS

U.S. Appl. No. 15/435,607, filed Feb. 17, 2017.
U.S. Appl. No. 15/435,631, filed Feb. 17, 2017.
Design U.S. Appl. No. 29/594,332, filed Feb. 17, 2017.
Design U.S. Appl. No. 29/594,340, filed Feb. 17, 2017.
European Search Report, Partial, and Provisional Written Opinion dated Jun. 27, 2018 for Application No. EP 18157199.3, 14 pgs.
European Search Report and Written Opinion dated Oct. 4, 2018 for Application No. EP 18157199.3, 13 pgs.
International Search Report and Written Opinion dated Jul. 20, 2018 for Application No. PCT/US2018/018104, 21 pgs.
European Examination Report dated Sep. 5, 2019 for Application No. EP 18157199.3, 4 pgs.

* cited by examiner

SURGICAL STAPLER WITH COOPERATING DISTAL TIP FEATURES ON ANVIL AND STAPLE CARTRIDGE

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, issued as U.S. Pat. No. 8,408,439 on Apr. 3, 2013; and U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2013. The disclosure of each of the above-cited U.S. Patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
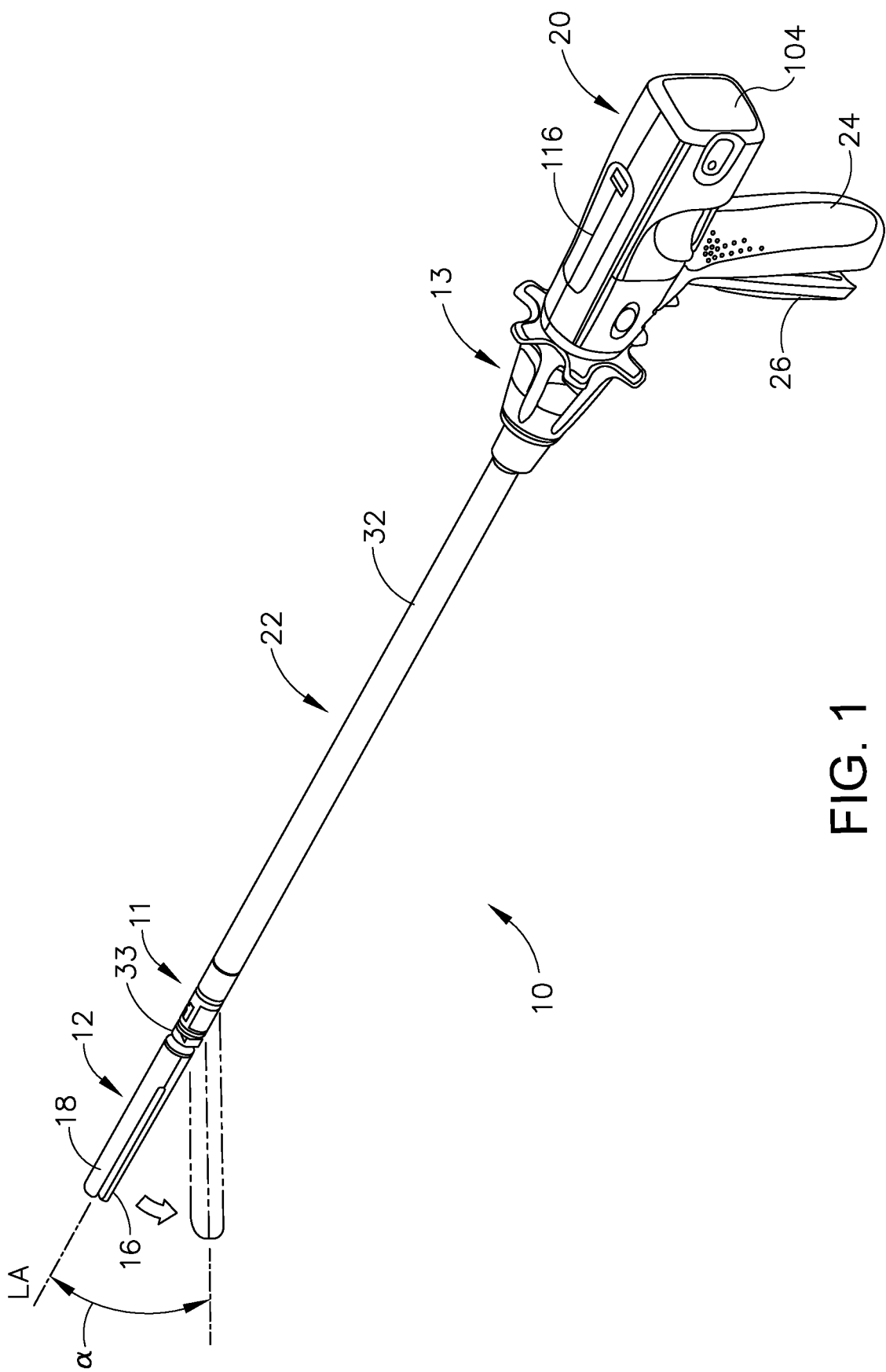
FIG. 1 depicts a perspective view of an exemplary articulating surgical stapling instrument.
Figure 2:
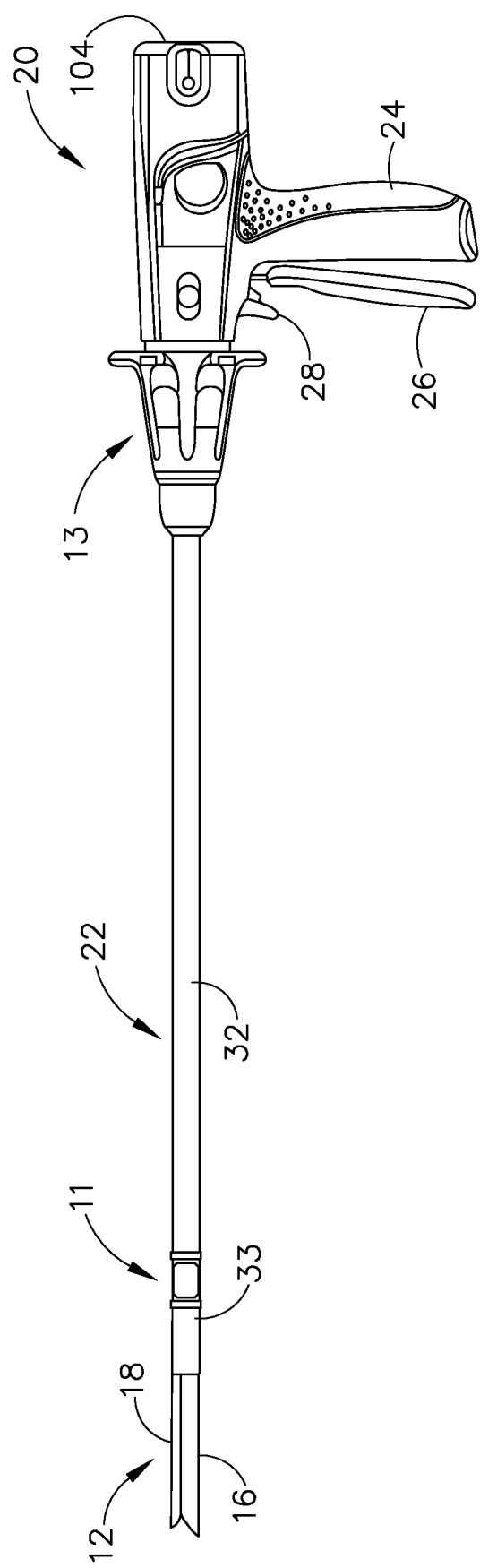
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. By way of further example only, shaft (22) may be detachable from handle portion (20) in accordance with at least some of the teachings of U.S. Pub. No. 2015/0272575, entitled "Surgical Instrument Comprising a Sensor System," published Oct. 1, 2015, issued as U.S. Pat. No. 9,913,642 on Mar. 13, 2018, the disclosure of which is incorporated by reference herein. In some other versions, shaft (22) is not detachable from handle portion (20). Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein. Articulation joint (11) may also be constructed and operable in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In some versions, lower jaw (16) is constructed in accordance with at least some of the teachings of U.S. Pub. No. 2014/0239044, entitled "Installation Features for Surgical Instrument End Effector Cartridge," published on Aug. 28, 2014, issued as U.S. Pat. No. 9,808,248 on Nov. 7, 2017, the disclosure of which is incorporated by reference herein. Anvil (18) may be constructed in accordance with at least some of the teachings of U.S. Pub. No. 2014/0239042, entitled "Integrated Tissue Positioning and Jaw Alignment Features for Surgical Stapler," published on Aug. 28, 2014, issued as U.S. Pat. No. 9,517,065 on Dec. 13, 2016, the disclosure of which is incorporated by reference herein; at least some of the teachings of U.S. Pub. No. 2014/0239036, entitled "Jaw Closure Feature for End Effector of Surgical Instrument," published on Aug. 28, 2014, issued as U.S. Pat. No. 9,839,421 on Dec. 12, 2017, the disclosure of which is incorporated by reference herein; and/or at least some of the teachings of U.S. Pub. No. 2014/0239037, entitled "Staple Forming Features for Surgical Stapling Instrument," published on Aug. 28, 2014, issued as U.S. Pat. No. 10,092,292 on Oct. 9, 2018, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. Pub. No. 2014/0239041, entitled "Lockout Feature for Movable Cutting Member of Surgical Instrument," published on Aug. 28, 2014, issued as U.S. Pat. No. 9,717,497 on Aug. 1, 2017, the disclosure of which is incorporated by reference herein. Other suitable forms that firing beam (14) may take will be apparent to those of ordinary skill in the art in view of the teachings herein.

Figure 3:
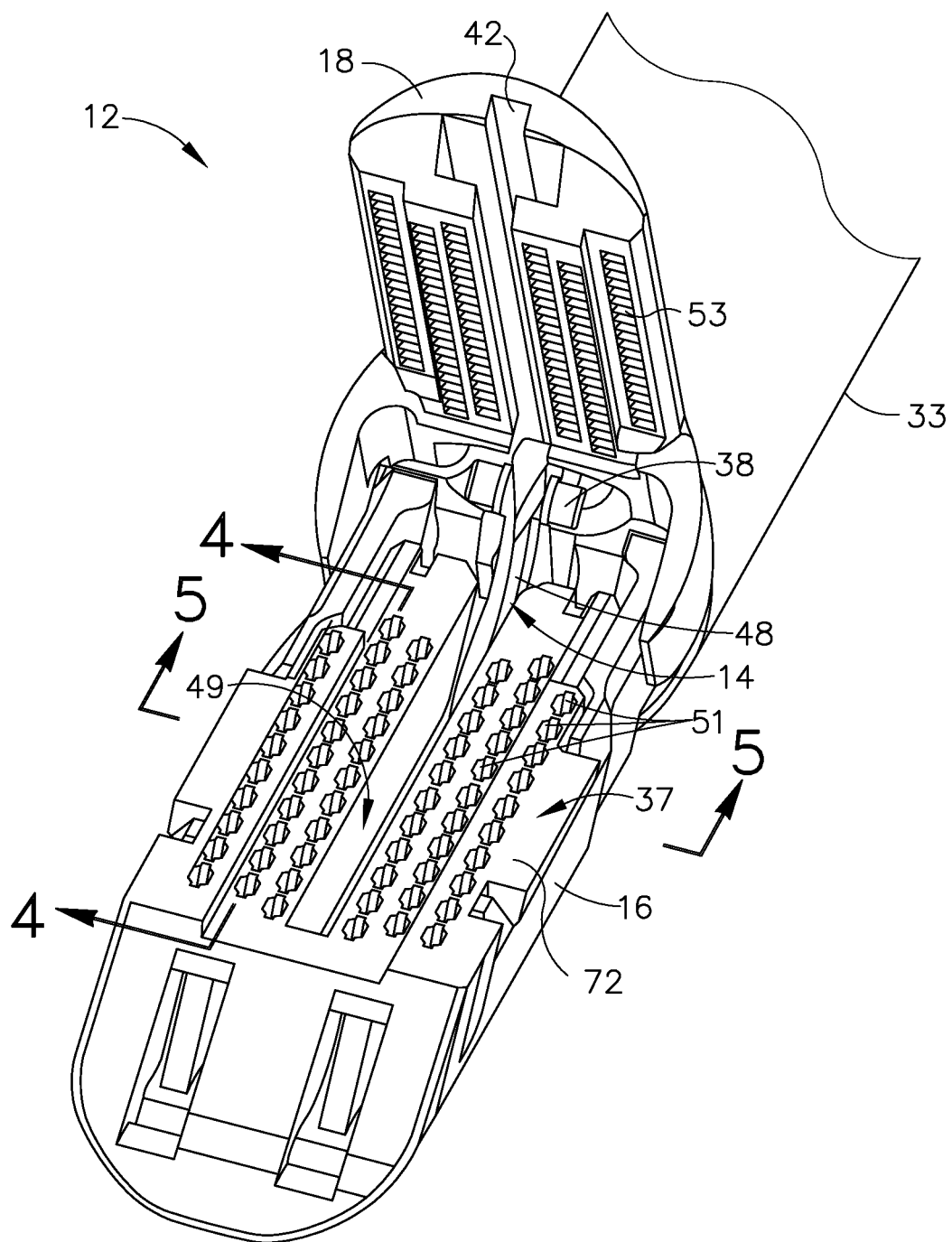
FIG. 3 depicts a perspective view of an opened end effector of the instrument of FIG. 1.
Figure 4A:
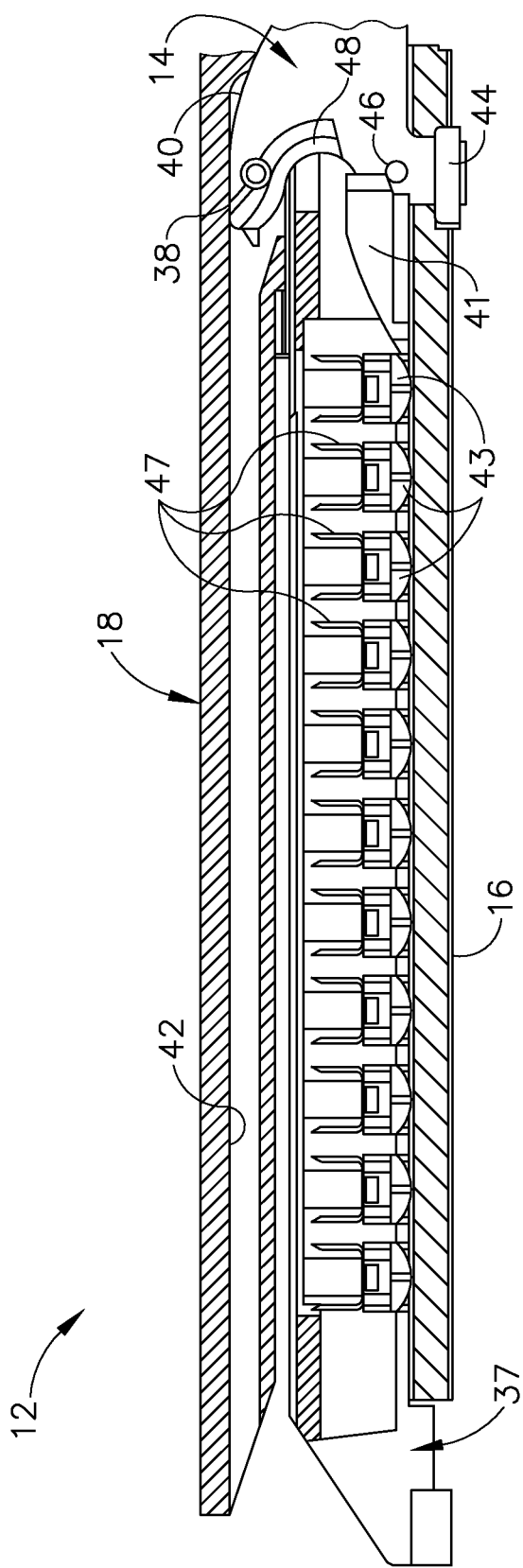
FIG. 4A depicts a side cross-sectional view of the end effector of FIG. 3, taken along line 4-4 of FIG. 3, with the firing beam in a proximal position.
Figure 4B:
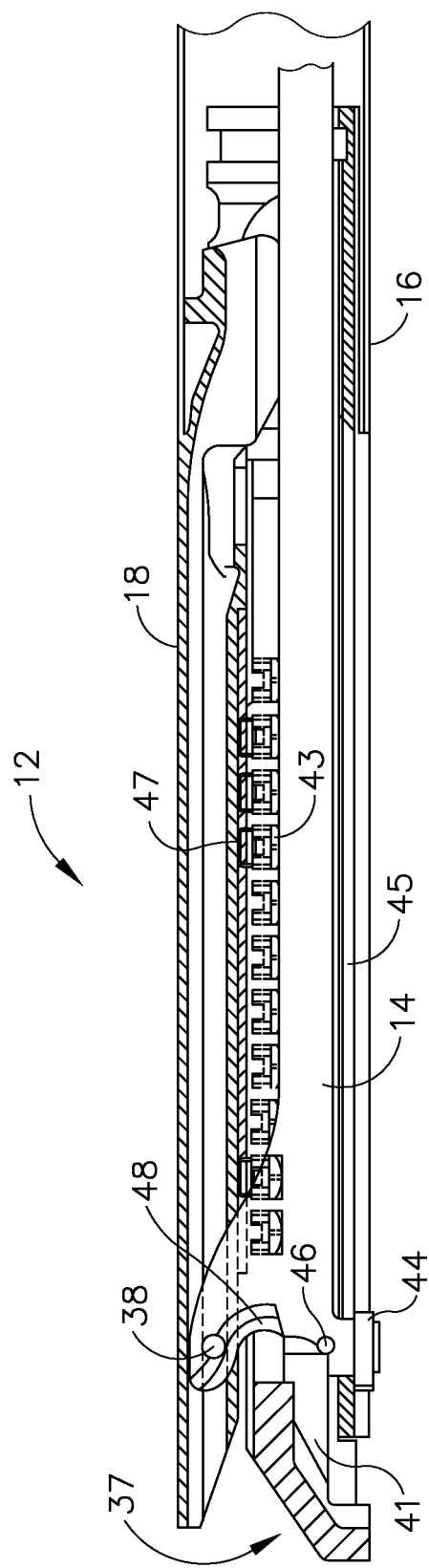
FIG. 4B depicts a side cross-sectional view of the end effector of FIG. 3, taken along line 4-4 of FIG. 3, with the firing beam in a distal position.
Figure 5:
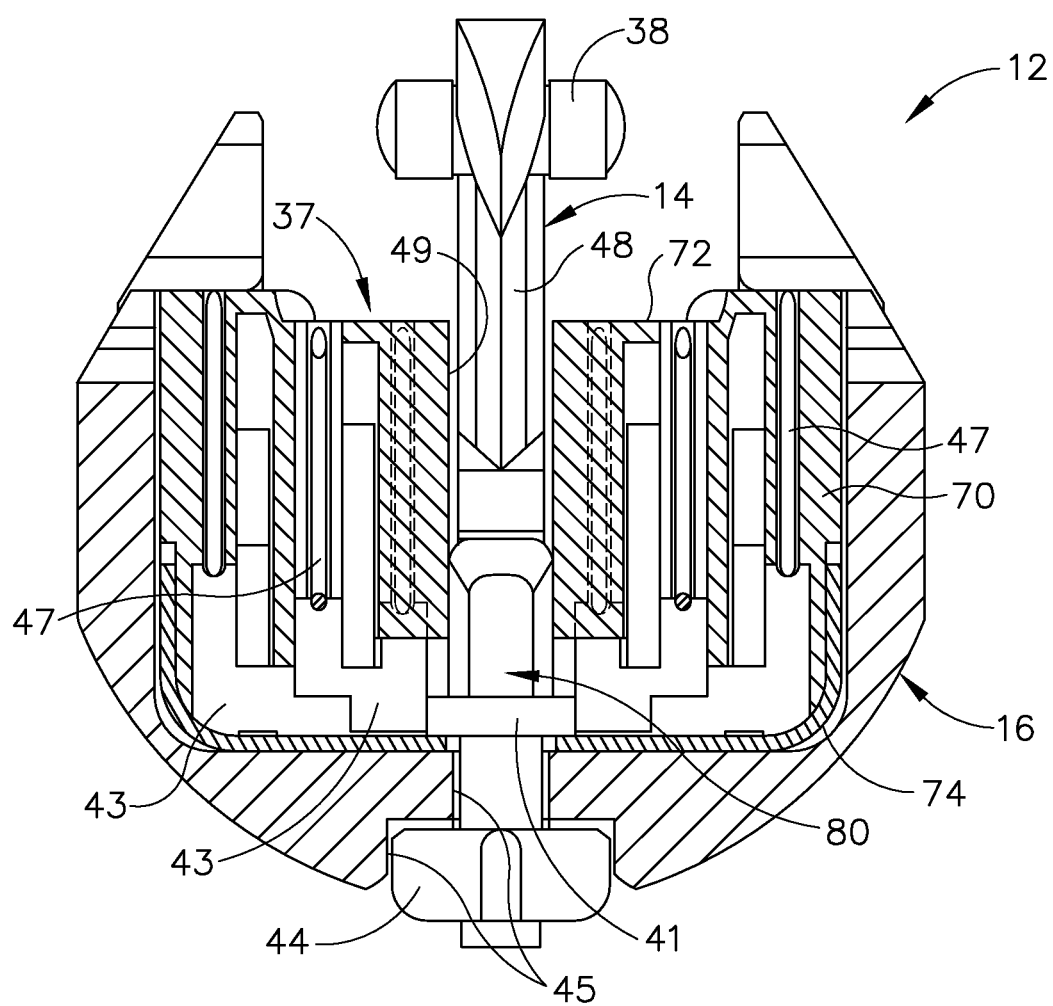
FIG. 5 depicts an end cross-sectional view of the end effector of FIG. 3, taken along line 5-5 of FIG. 3.
Figure 6:
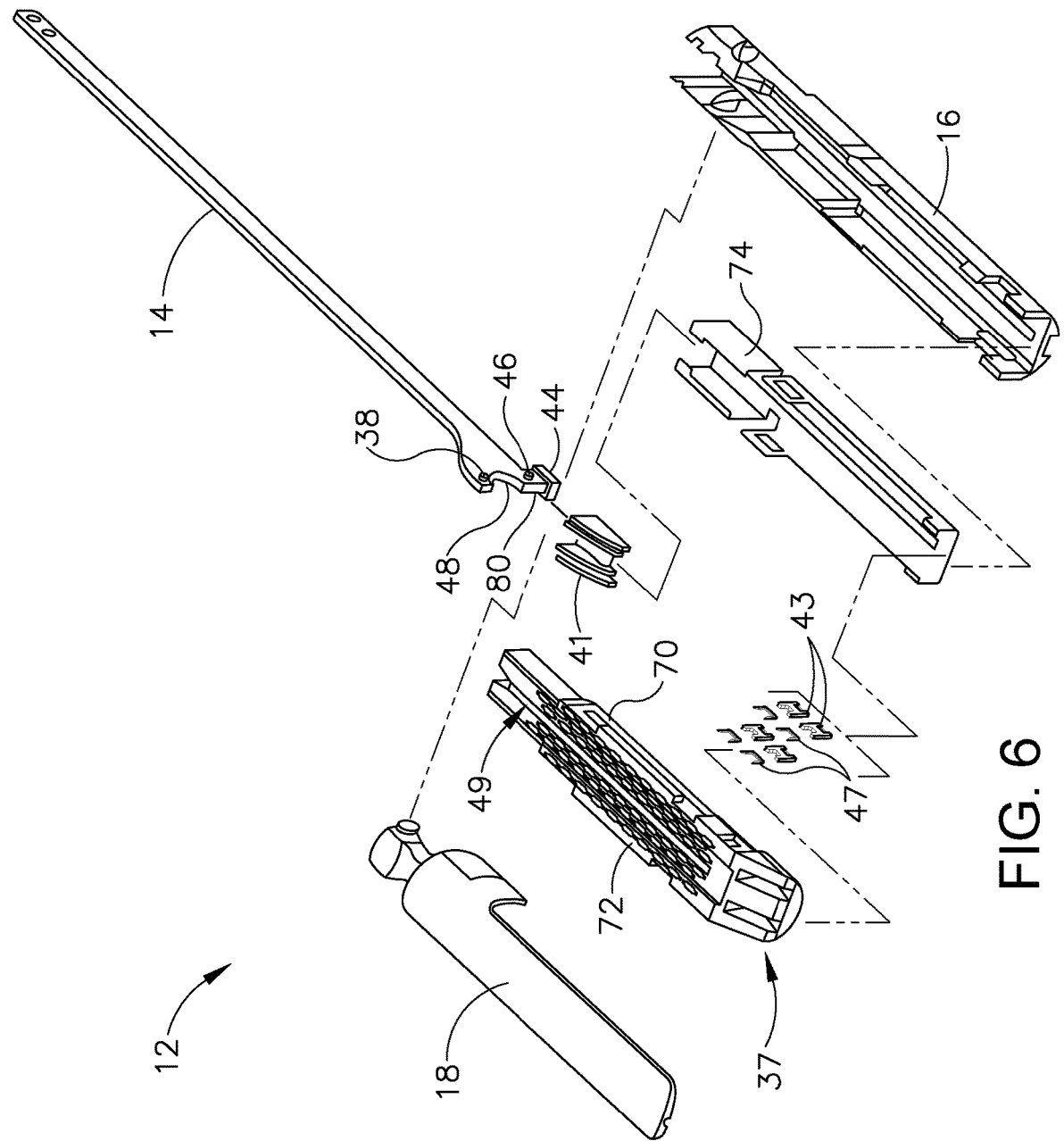
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. Pub. No. 2014/0239042, entitled "Integrated Tissue Positioning and Jaw Alignment Features for Surgical Stapler," published on Aug. 28, 2014, issued as U.S. Pat. No. 9,517,065 on Dec. 13, 2016, the disclosure of which is incorporated by reference herein. In addition or in the alternative, staple cartridge (37) may be constructed and operable in accordance with at least some of the teachings of U.S. Pub. No. 2014/0239044, entitled "Installation Features for Surgical Instrument End Effector Cartridge," published on Aug. 28, 2014, issued as U.S. Pat. No. 9,808,248 on Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
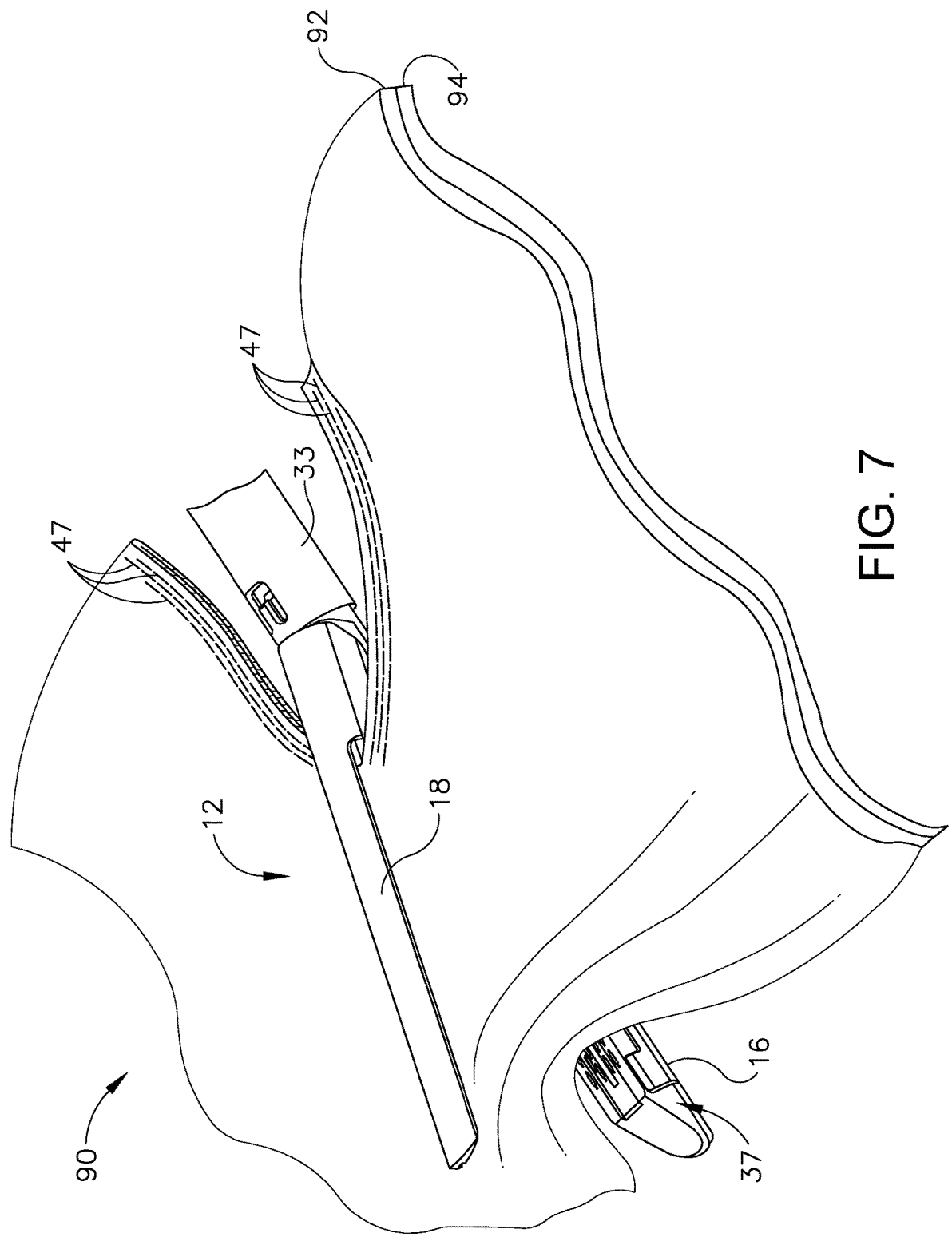
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

In one version, instrument (10) provides motorized control of firing beam (14). Exemplary components that may be used to provide motorized control of firing beam (14) are shown and described in US. Pub. No. 2014/0239043, entitled "Distal Tip Features for End Effector of Surgical Instrument," published on Aug. 28, 2014, issued as U.S. Pat. No. 9,622,746 on Apr. 18, 2017, the disclosure of which is incorporated by reference herein. In addition to or in lieu of the foregoing, at least part of the motorized control may be configured in accordance with at least some of the teachings of U.S. Pat. No. 8,210,411, entitled "Motor-Driven Surgical Instrument," issued Jul. 3, 2012, the disclosure of which is incorporated by reference herein. In addition to or in lieu of the foregoing, the features operable to drive firing beam (14) may be configured in accordance with at least some of the teachings of U.S. Pub. No. 2012/0239012, issued as U.S. Pat. No. 8,453,914 on Jun. 4, 2013, the disclosure of which is incorporated by reference herein; and/or in accordance with at least some of the teachings of U.S. Pub. No. 2012/0239012, issued as U.S. Pat. No. 8,453,914 on Jun. 4, 2013, the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

Instrument (10) may also include a lockout switch and lockout indicator as shown and described in US. Pub. No. 2014/0239043, entitled "Distal Tip Features for End Effector of Surgical Instrument," published on Aug. 28, 2014, issued as U.S. Pat. No. 9,622,746 on Apr. 18, 2017, the disclosure of which is incorporated by reference herein. Additionally, a lockout switch and/or lockout indication and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Instrument (10) also include a manual return switch (116) configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide further functionality in accordance with at least some of the teachings of U.S. Pub. No. 2014/0239043, entitled "Distal Tip Features for End Effector of Surgical Instrument," published on Aug. 28, 2014, issued as U.S. Pat. No. 9,622,746 on Apr. 18, 2017, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

It should be understood that instrument (10) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; 7,721,930; U.S. Pub. No. 2010/0264193, issued as U.S. Pat. No. 8,408,439 on Apr. 2, 2013; and/or 2012/0239012, issued as U.S. Pat. No. 8,453,914 on Jun. 4, 2013. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary End Effector with Visualization, Lead-in, and Gathering Features

In some instances, it may be desirable to provide the user with better visualization of end effector (12). In particular, as end effector (12) is inserted into a surgical site, the user may rotate shaft (22) of instrument (10) during the procedure. As a result, end effector (12) also rotates. As end effector (12) rotates, it may be desirable for the user to have visual access to the surgical site. For instance, the user may wish to see the interface or contact between tissue (90) and end effector (12). Since end effector (12) may be rotated about the longitudinal axis (LA) relative to handle portion (20), the user may view the surgical site such that lower jaw (16) of end effector is visible rather than anvil (18). Alternatively, end effector (12) could be rotated such that when the user views end effector (12), anvil (18) is visible by the user. It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (12) has been positioned properly within the surgical site for anvil (18) and lower jaw (16) to fully clamp the vessel. One potential way of monitoring the surgical site may include improving visualization of the area adjacent to the distal tip of lower jaw (16) and anvil (18). Furthermore, not only visualization of the distal end of end effector (12) may be desirable, but also it may be desirable to construct end effector (12) such that the distal end of anvil (18) is configured to urge tissue (e.g., a large vessel) proximally into the space between anvil (18) and lower jaw (16) as anvil (18) closes toward lower jaw (16).

Figure 8:
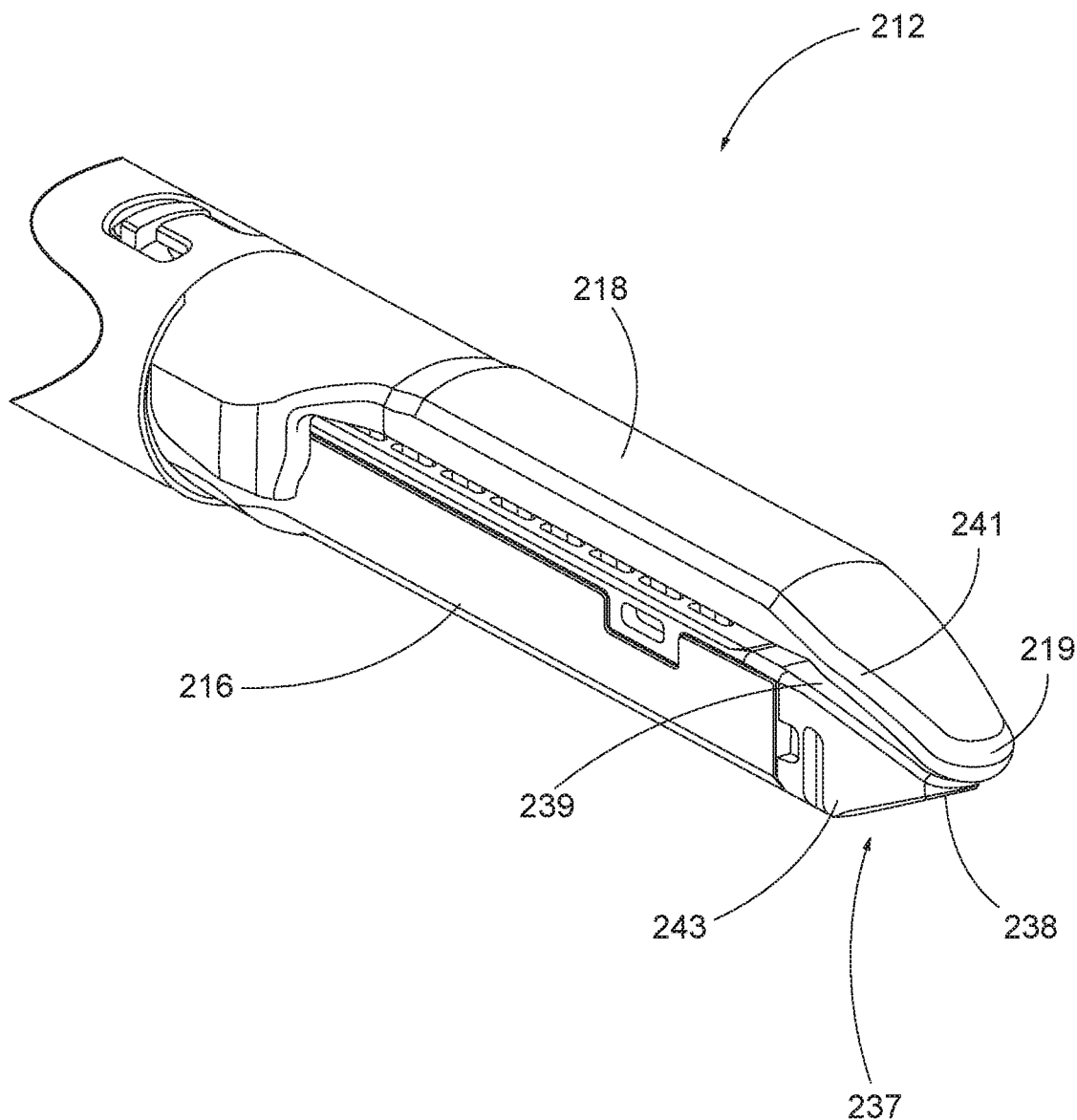
FIG. 8 depicts a perspective view of an alternative version of an end effector with an angled anvil and an angled cartridge.

FIG. 8 depicts an exemplary end effector (212) comprising an anvil (218) and a lower jaw (216). It will be appreciated that end effector (212) may be used in place of end effector (12) of instrument (10). End effector (212) may be integrally formed with instrument (10) or in the alternative may be interchangeable with end effector (12) of instrument (10).

Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 9:
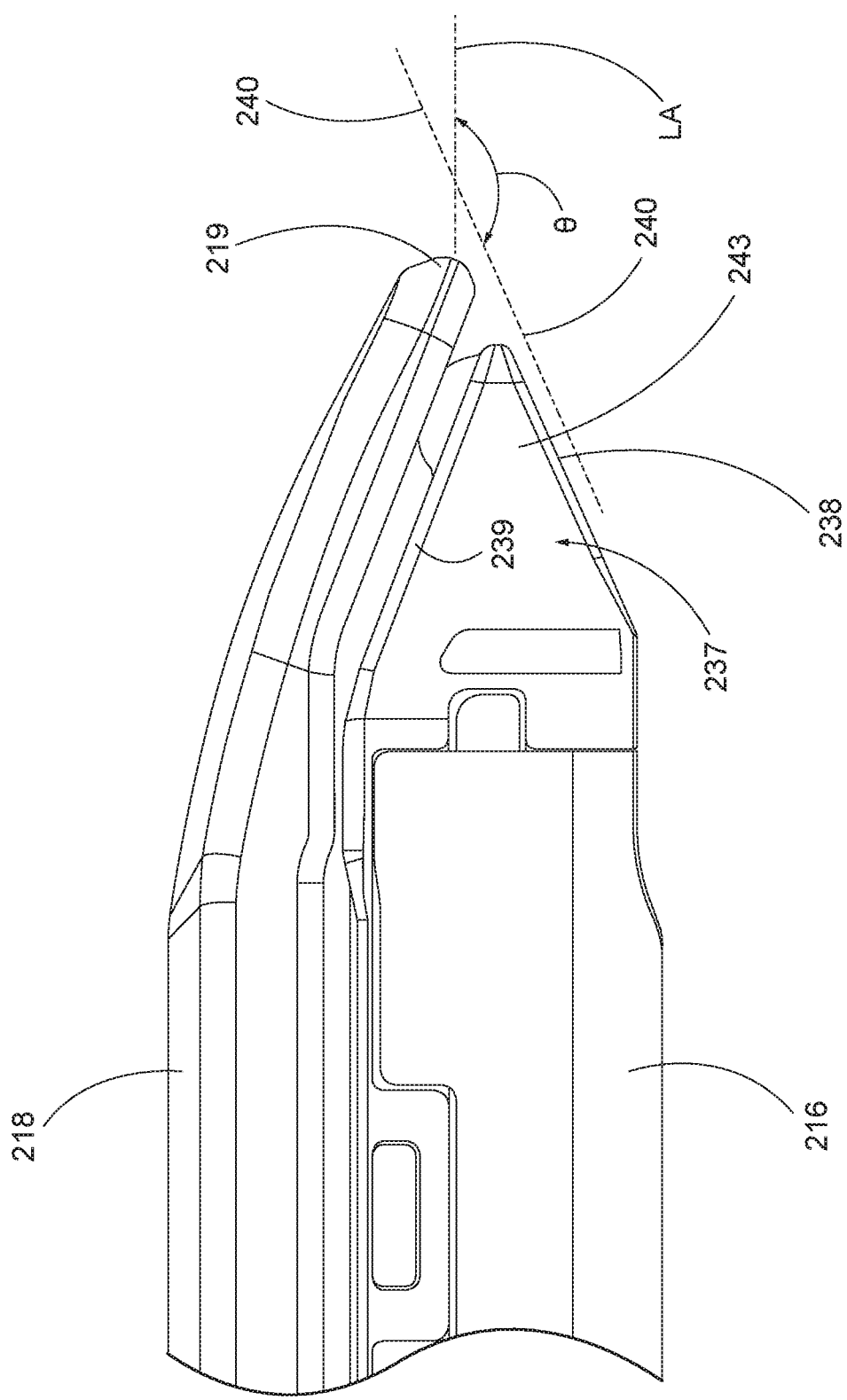
FIG. 9 depicts an enlarged, side view of the end effector of FIG. 8.
Figure 10:
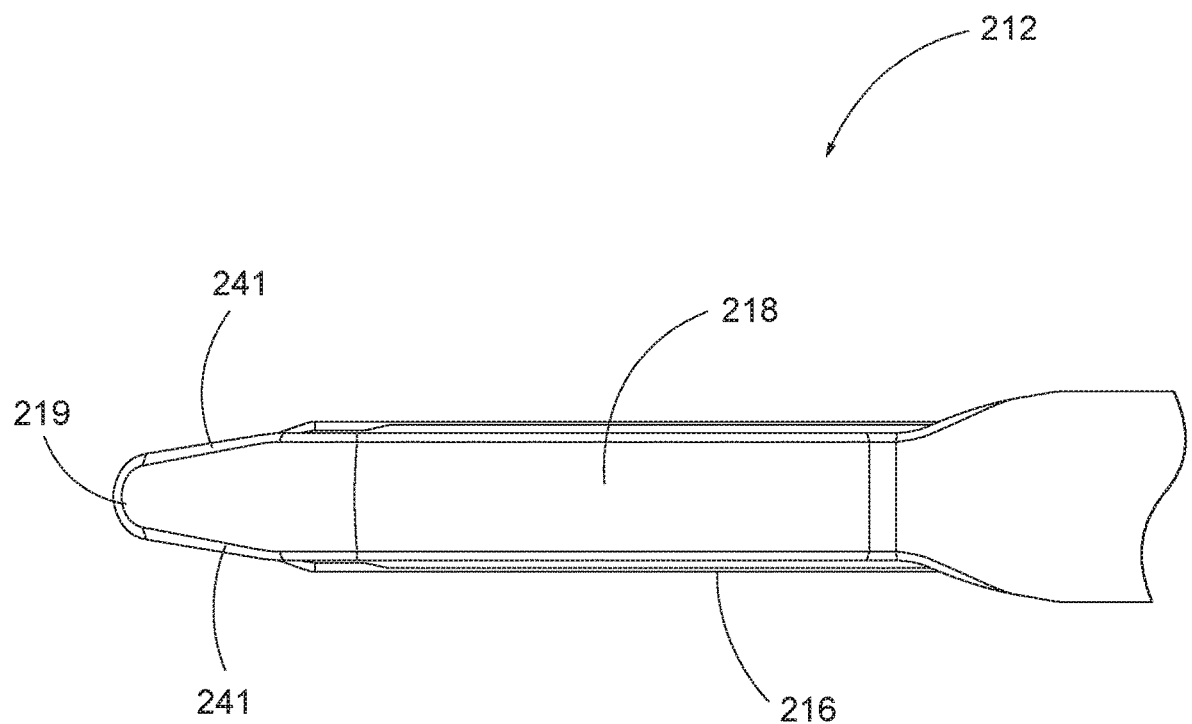
FIG. 10 depicts an enlarged top view of the end effector of FIG. 8.

Anvil (218) as can be seen in FIGS. 8-10 has an elongated shape where the distal portion of anvil (218) angles toward cartridge (237). The distal portion of anvil (218) angles toward cartridge (237) such that the distal most tip (219) of anvil (218) extends distally longitudinally further than cartridge (237). Though in some versions, distal tip (219) may extend to a distance longitudinally equal to cartridge (237) or proximal relative to the distal most point on cartridge (237). Furthermore, anvil (218) angles toward cartridge (237) through a gentle slope. As seen best in FIG. 10, anvil (218) includes sides (241) that taper as they approach the distal most tip (219) of anvil (218). By way of example, anvil (218) is shaped in FIG. 8 similarly to an inverted ski tip. The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site. Other suitable variations of anvil (218) will be apparent to one of ordinary skill in the art in view of the teachings herein.

Cartridge (237) is operable to hold staples similar to staples (47) shown in FIG. 4A for driving into tissue. As shown in FIG. 9, the distal end of cartridge (237) has a triangular profile. In particular, the distal end of cartridge (237) comprises an upper tapered surface (239) and a lower tapered surface (238). Additionally, the distal end of cartridge (237) comprises a tapered side surface (243) on each side. In the present example, each tapered side surface (243)

of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). It will be appreciated that the planar shape of lower tapered surface (238) may be operable to allow the user to visualize and/or nearly visualize the distal tip (219) of anvil (218). In particular, sight line (240) intersects longitudinal axis (LA), which extends longitudinally through end effector (212), to form a viewing angle ($\theta$).

Viewing angle ($\theta$) may establish the relative visibility that a user has regarding distal tip (219). In particular, the user can see in front of distal tip (219) along any line of sight that passes through the intersection of sight line (240) and longitudinal axis (LA) within viewing angle ($\theta$). For instance, as viewing angle ($\theta$) increases, the user would have greater visibility of the area immediately in front of distal tip (219) from proximal vantage points; whereas as viewing angle ($\theta$) decreases, the user has less visibility of the area in front of distal tip (219) from proximal vantage points. In some versions, viewing angle ($\theta$) defines an angle greater than 90 degrees. Additionally, in some versions, viewing angle ($\theta$) defines an angle greater than 135 degrees. Other suitable angles for viewing angle ($\theta$) will be apparent to one of ordinary skill in the art in view of the teachings herein. In the illustrated version, the user generally looks along sight line (240) or along some other line of sight within viewing angle ($\theta$), thus, the user has visibility along sight line as well as any area within viewing angle ($\theta$). The underside of distal tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle ($\theta$) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90).

It will be appreciated that in some instances, end effector (212) may be rotated before, during, or after clamping tissue (90). As a result, the tapered shape of anvil (218) may also provide more accessible viewing of distal tip (219) or substantially adjacent distal tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). For instance, once distal tip (219) is fit into a trocar, lower tapered surface (238) and the tapered shape of anvil (218) may provide a lead-in, guiding the rest of end effector (212) into the trocar. In view of the teachings herein, those of ordinary skill in the art will further appreciate that visibility and maneuverability can be enhanced by the tapered design for both sides (241) of anvil (218) and each side (243) of cartridge (237).

In addition to the foregoing, end effector (212) and versions of instrument (10) incorporating end effector (212) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pub. No. 2014/0239041, entitled "Lockout Feature for Movable Cutting Member of Surgical Instrument," published Aug. 28, 2014, issued as U.S. Pat. No. 9,717,497 on Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; U.S. Pub. No. 2014/0239043, entitled "Distal Tip Features for End Effector of Surgical Instrument," published Aug. 28, 2014, issued as U.S. Pat. No. 9,622,746 on Apr. 18, 2017, the disclosure of which is incorporated by reference herein; U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein; U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein; and/or U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Further modifications that may be incorporated into end effector (212) will be described in greater detail below.

III. End Effector with Cooperating Features on Curved Anvil Tips and Cartridge Noses In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (10) may be placed at the surgical site, actuated to cut and staple, then removed from the surgical site for installing a new cartridge (37), and then be placed back at the surgical site again for the next cut and staple along the same path in which the previous cutting and stapling cycle occurred. This process is repeated until the cut and staple procedure is complete. As can be seen in FIGS. 4A-4B and FIG. 7, the distal end configuration of end effector (12) provides a gap between the distal end of anvil (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12), with the different configuration of end effector (212) providing different potential advantages. In particular, the distal end configuration of end effector (212) may provide improved maneuverability and improved visibility of the relationship between the distal end of end effector (212) and adjacent anatomical structures. In addition, the distal end configuration of end effector (212) may provide tissue-gathering effects by urging tissue proximally into the space between anvil (218) and lower jaw (216) as anvil (218) is closed toward lower jaw (216). However, in versions where all the structures of end effector (212) are rigid, the bent configuration of distal tip (219) of anvil (218) may not lend itself well to marching operations, as distal tip (219) may impart trauma to tissue that is not gathered into the space between anvil (218) and lower jaw (216) as anvil (218) is closed toward lower jaw (216). Thus, in versions where all the structures of end effector (212) are rigid, end effector (212) may be best suited for cutting and stapling operations (e.g., vessel transection) where all of the tissue that is to be cut and stapled is gathered proximal to distal tip (219).

In view of the foregoing, it may be desirable to provide a variation of end effectors (12, 212) that provides the marching capabilities of end effector (12), the improved visibility associated with end effector (212), and the tissue gathering capabilities of end effector (212), without providing an increased risk of trauma that might otherwise be associated with fully rigid versions of end effector (212). The following describes several merely illustrative examples of such variations of end effectors (12, 212). In the following examples, an anvil has a distal tip that is resiliently biased to assume a bent or angled configuration like distal tip (219); yet the resiliently biased distal tip is deflectable away from the lower jaw in response to a sufficient load on the distal tip. It will be understood in view of the teachings herein that providing an anvil with an elastically deformable angled distal tip portion can provide an additional level of maneuverability benefits in terms of navigating through tissue to a surgical site. In this manner, the deformable distal tip portion may deflect or deform to promote smooth and atraumatic movement of the end effector through tissue, particularly during marching operations. Additionally, with an anvil having a bias to an angled position when not in a loaded state or contacted by surrounding tissue, enhanced visualization during tissue capture and cutting can be achieved compared to using end effectors with a straight or non-angled anvil. Moreover, an anvil with a distal tip that is biased to an angled position may provide some degree of tissue gathering effects up until reaching a load point that would be associated with marching rather than being associated with simply gathering a relatively small tissue structure between the anvil and lower jaw.

Some exemplary end effectors having curved anvil tips that are elastically deformable are described in U.S. patent application Ser. No. 15/435,573, entitled "Surgical Stapler with Elastically Deformable Tip," filed on Feb. 17, 2017, published as U.S. Pub. No. 2018/0235609 on Aug. 23, 2018, the disclosure of which is incorporated by reference herein. One exemplary way to provide anvils for end effectors that provide better visualization and maneuverability characteristics is to configure an anvil with a modular curved tip, that may also be elastically deformable. Some exemplary anvils having modular curved tips, and that may be elastically deformable, are described in U.S. patent application Ser. No. 15/435,607 entitled "Surgical Stapler with Insertable Distal Anvil Tip," filed on Feb. 17, 2017, issued as U.S. Pat. No. 10,729,434 on Aug. 4, 2020, and the disclosure of which is incorporated by reference herein.

As will be described further below, with end effectors that incorporate modular releasable anvil tips where the tips may be elastically deformable, enhanced tissue gripping can be achieved using end effectors having anvil tips and cartridge noses with cooperating features. Such cooperating features may provide a lock or tissue stop that prevents clamped tissue from moving out of the distal end of the end effector during a cutting and stapling action. Such cooperating features may also act as a tactile feedback feature to signal to a user that they have completely clamped the tissue, vessel, or tubular structure by feeling the cooperating features engage or contact at the distal end. In marching applications, such cooperating features can similarly act as a feedback feature or structure to signal to a user that they are at the end of the tissue path, as evidenced by the cooperating features engaging or contacting at the distal end (as opposed to the respective cooperating features each contacting tissue). Additionally, as described further below, to ensure that the matching anvil tips and cartridges tips are used together, such anvil tips and cartridges with cooperating features can be provided as a kit with a loading and/or unloading cartridge or tool.

Figure 11:
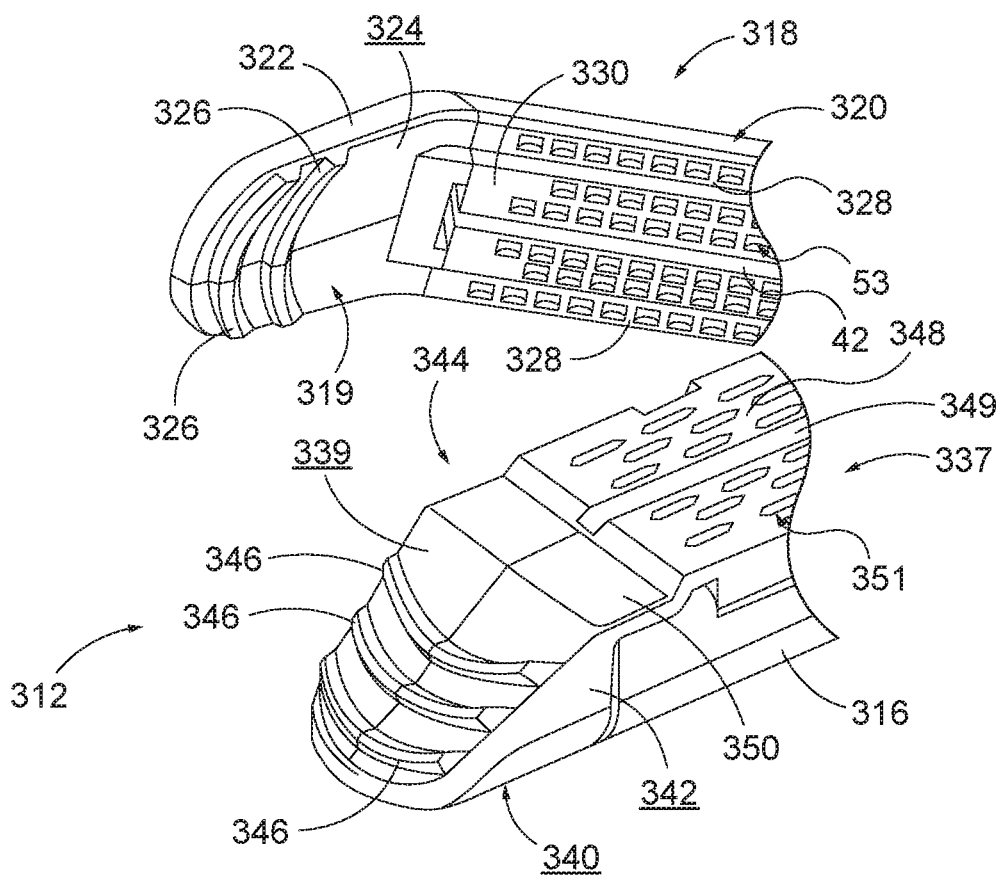
FIG. 11 depicts an enlarged exploded perspective view of a distal portion of an alternative version of an end effector, with a curved anvil tip and cartridge nose having cooperating features.

A. Curved and Deformable Anvil Tips and Rigid Cartridge Noses Each with Cooperating Raised Ribs FIG. 11 depicts an exemplary end effector (312) comprising an anvil (318) and a lower jaw (316). It will be appreciated that end effector (312) may be used in place of end effector (12) of instrument (10). End effector (312) may be integrally formed with instrument (10) or in the alternative may be interchangeable with end effector (12) of instrument (10). Anvil (318) is operable to pivot relative to lower jaw (316). Anvil (318) and lower jaw (316) may clamp tissue (90) similarly to clamping performed by anvil (18) and lower jaw (16) shown in FIG. 1. End effector (312) further comprises a cartridge (337) that is operable to be placed in lower jaw (316) similarly to cartridge (37) shown in FIG. 3.

Anvil (318) comprises an anvil body (320) and an anvil tip (319). Anvil (318) has an elongated shape where anvil body (320) is straight and anvil tip (319) extends distally in an angled or curved manner toward cartridge (337). Anvil tip (319) includes sides (322) that taper as they approach the distal-most part of anvil tip (319), although such a tapered configuration is not required in all versions. By way of example, anvil (318) is shaped in FIGS. 11 and 12 with the shape of anvil tip (319) being similar to an inverted ski tip. This may provide easier insertion of end effector (312) into a surgical site. For instance, the gentle slope or inverted ski tip shape of anvil tip (319) may provide an atraumatic tissue deflection surface as anvil (318) contacts or moves through tissue. Once placed into a surgical site, the angled shape of anvil tip (319) may provide better maneuverability of end effector (312). Other suitable variations of anvil (318) will be apparent to one of ordinary skill in the art in view of the teachings herein.

As used herein, the terms "angled" and "curved" shall be read as being synonymous with each other when referring to a distal end configuration of a component of an end effector. In other words, the term "curved" (and variations thereof) may include a relationship between two straight features that together define an angle, such that the term "curved" (and variations thereof) should not be read as requiring a component to necessarily extend along an arc.

Anvil (318) further comprises staple forming pockets (53) as described above; and longitudinal anvil slot (42) as also described above. In the present example, and as more clearly shown from FIG. 12, anvil tip (319) is configured as a modular releasable component that selectively connects with or attaches to anvil body (320). In the present example, anvil tip (319) comprises an insert or other structure that extends proximally and is configured to be received within a distal end of longitudinal slot (42). Some exemplary structures and ways to connect a modular releasable anvil tip with an anvil body are shown and described in U.S. patent application Ser. No. 15/435,607 entitled "Surgical Stapler with Insertable Distal Anvil Tip," filed on Feb. 17, 2017, issued as U.S. Pat. No. 10,729,434 on Aug. 4, 2020, and the disclosure of which is incorporated by reference herein. Still yet, other ways to connect anvil tip (319) with anvil body (320) will be apparent to those of ordinary skill in the art in view of the teachings herein.

Anvil tip (319) comprises a bottom surface (324) that faces cartridge (337) and that is configured to contact tissue (90) when end effector (312) is in a loaded state clamping tissue (90). Along bottom surface (324), anvil tip (319) comprises one or more features (326) that are configured to also contact tissue (90) when end effector (312) is in a loaded state. In the present example, one or more features (326) comprise a pair of raised arcuate ribs that generally extend transversely across a width of anvil tip (319). In this manner, the raised arcuate ribs protrude or extend from bottom surface (324) toward cartridge (337). While the present example shows two such ribs, in other versions anvil tip (319) comprises greater or fewer ribs. Also, in the present example, one or more features (326) are positioned along or closer to a distal end of anvil tip (319) rather than along a proximal end of anvil tip (319). In some other versions, however, one or more features (326) can be located along a middle portion, proximal end, or other portions of bottom surface (324) of anvil tip (319).

Anvil tip (319) is comprised of an elastomeric material in the present example. With such a construction, in use during clamping tissue, anvil tip (319) may deflect or bend from a curved state to a straight or less curved state. By way of example only, tip (319) may be deflectable between about 20 degrees and about 70 degrees in a downward direction from a longitudinal axis toward cartridge; between about 0 degrees and about 90 degrees in an upward direction from a longitudinal axis toward cartridge (337). The degree of deflection may be influenced by the thickness and/or density of the tissue that is being compressed between anvil (318) and cartridge (337). In addition, or in the alternative, anvil tip (319) may deflect or bend from a curved state to a straight or less curved state in accordance with at least some of the teachings in U.S. patent application Ser. No. 15/435,573, entitled "Surgical Stapler with Elastically Deformable Tip," filed on Feb. 17, 2017, published as U.S. Pat. No. 2018/0235609 on Aug. 23, 2018, the disclosure of which is incorporated by reference herein. As described above, in this manner anvil tip (319) is operably configured for use in procedures where marching is used. Furthermore, one or more features (326) are similarly formed of an elastomeric material such that they are also elastically deformable. In some versions, one or more features (326) are elastically deformable to a different extent than anvil tip (319) generally. However, in other versions, one or more features (326) can be elastically deformable to the same or to a greater extent compared to anvil tip (319) generally. In view of the teachings herein, various ways to modify and manipulate the degree or extent of elastic deformability of one or more features (326) and/or anvil tip (319) generally will be apparent to those of ordinary skill in the art. Still in other versions, anvil tip (319) and/or its one or more features (326) are not required to be elastically deformable and thus may be rigid.

Cartridge (337) is operable to hold staples similar to staples (47) shown in FIG. 4A for driving into tissue. In the present example, cartridge (337) comprises a nose portion (344) at a distal end. Cartridge nose (344) has a triangular profile. In particular, cartridge nose (344) comprises an upper tapered surface (339), a bottom surface (340), and side surfaces (342). In the present example, bottom surface (340) is generally parallel with a longitudinal axis defined by cartridge (337). In some other examples, bottom surface (340) is angled toward the longitudinal axis defined by cartridge (337), similar to the configuration shown above with respect to cartridge (237).

Along upper surface (339), cartridge (337) comprises one or more features (346) that are configured to also contact tissue (90) when end effector (312) is in a loaded state. In the present example, one or more features (346) comprise a pair of raised arcuate ribs that generally extend transversely across a width of cartridge (337). In this manner, the raised arcuate ribs protrude or extend from upper surface (339) toward anvil tip (319). While the present example shows three such ribs, in other versions nose portion (344) of cartridge (337) comprises greater or fewer ribs. Also, in the present example, one or more features (346) are positioned along or closer to a middle and distal end of nose portion (344) rather than along a proximal end of nose portion (344). In some other versions, however, one or more features (346) can be located along a proximal end, or other portions of upper surface (339) of cartridge (337).

In the present version, cartridge (337) and one or more features (346) protruding from nose portion (344) are rigid such that they do not elastically deform when end effector (312) is in a loaded state clamping tissue (90). Furthermore, when end effector (312) is closed and in a non-loaded state not clamping tissue, one or more features (346) of cartridge (337) are configured to complement one or more features (326) of anvil tip (319). In this manner, when tissue (90) is not present within end effector (312), one or more features (346) of cartridge (337) and one or more features (326) of anvil tip (319) cooperate to form a nesting arrangement. In this nesting arrangement, one or more features (326) of anvil tip (319) are positionable adjacent to one or more features (346) of cartridge (337). In the illustrated version of FIG. 11, when nested, a distal-most rib of anvil tip (319) is positioned adjacent to and proximal to a distal-most rib of cartridge (337). In other versions where a nesting arrangement exists, a distal-most rib of anvil tip (319) is positioned adjacent to and distal to a distal-most rib of cartridge (337).

With the arrangement described above and as illustrated in FIG. 11, end effector (312) comprises the combination of elastically deformable anvil tip (319) having one or more features (326), combined with rigid cartridge nose (344) having one or more features (346). Furthermore, as described above the one or more features (326) cooperate with, or are complementary to, the one or more features (346). In other versions, one or more features (346) of cartridge nose (344) can be configured as elastically deformable while one or more features (326) of anvil tip (319) can be configured as rigid. Still yet in other versions, both of one or more features (326, 346) can be elastically deformable, or both can be rigid.

With end effector (312), bottom surface (324) of anvil tip (319) and upper surface (339) of cartridge nose portion (344) are generally parallel surfaces. This parallel orientation promotes equal nesting of one or more features (326) of anvil (319) with one or more features (346) of nose portion (344). For instance, in the present example, the most distal features (326, 346) will nest to the same extent or degree as the most proximal features (326, 346). Additionally, this parallel orientation provides for a consistent gap between those portions of anvil bottom surface (324) and cartridge upper surface (339) not having the one or more features (326, 346). In view of the teachings herein, other arrangements for the orientation of bottom surface (324) and upper surface (339), including non-parallel arrangements, will be apparent to those of ordinary skill in the art.

While the present example of FIG. 11 is described as one or more features (326) of anvil tip (319) and one or more features (346) of cartridge nose (344) adopting a nesting arrangement, in some instances such an arrangement may be a contacting arrangement where one or more features (326) of anvil tip (319) contact with upper surface (339) of cartridge nose (344) when end effector (312) is closed and in an unloaded state and/or one or more features (346) of cartridge nose (344) contact with bottom surface (324) of anvil tip (319) when end effector (312) is closed and in an unloaded state. In such a nested and contacting configuration, the gap between the flat regions of bottom surface (324) and upper surface (339) generally equals the distance that the protruding ribs extend away from their respective bottom surface (324) and upper surface (339). Some other nesting arrangements are non-contacting arrangements where, even when end effector (312) is closed and in an unloaded state where no tissue is within end effector (312), one or more features (326) of anvil tip (319) do not contact cartridge (337); and similarly one or more features (346) of cartridge nose (344) do not contact anvil tip (319). In a loaded state, regardless if the nesting arrangement is contacting or non-contacting, one or more features (326, 346) contact tissue in a manner that applies staggered concentrations of force to clamped tissue (90). These staggered concentrations of force coincide with the locations where one or more features (326, 346) that protrude from respective anvil tip (319) and cartridge nose (344) contact tissue (90).

In instances when anvil tip (319) and cartridge nose (344) have a contacting arrangement, in marching applications when tissue (90) is clamped between a closed cartridge (337) and anvil (318), a user would be able to determine whether they are at the final cut and staple location along the tissue since at that point the one or more features (326, 346) would engage in their nested arrangement. This could be detected by the user visually and/or based on tactile feedback from prior cut and staple iterations. In other applications where an entire tissue portion or vessel is supposed to be captured between a closed cartridge (337) and anvil (318), such confirmation and feedback can be provided in this manner as well. Furthermore, where a contacting nesting arrangement is used for anvil tip (319) and cartridge nose (344), the one or more features (326, 346) also provide a tissue stop or locking feature that prevents tissue (90) that is clamped between anvil (318) and cartridge (337) from spilling over the end of end effector (312).

It will be appreciated that in some instances, end effector (312) may be rotated before, during, or after clamping tissue (90). As a result, the curved shape of anvil (318) may also provide more accessible viewing of anvil tip (319) or regions substantially adjacent anvil tip (319). The curve of anvil (318) may further promote easy insertion of end effector (312) into tissue in an atraumatic manner. Furthermore, it may be easier to fit end effector (312) through a trocar or other devices operable to introduce end effector (312) into a surgical site due to the curve of anvil (318) of end effector (312).

Referring again to FIG. 11, cartridge (337) comprises vertical slot (349) having the same or similar structure and function as vertical slot (49) discussed above. Cartridge (337) also comprises staple apertures (351) having the same or similar structure and function as staple apertures (51) discussed above. In the present example, cartridge (337) is generally flat along a staple deck (348) with staple apertures (351) being along the same plane defined by staple deck (348). Distal to staple deck (348), cartridge (337) comprises shelf (350), which is also flat but is slightly recessed relative to staple deck (348). In view of the teachings herein, various modifications and other ways to configure cartridge (337) will be apparent to those of ordinary skill in the art. For instance, cartridge (337) may be modified similar to cartridge (37) above by having cartridge (337) include separate raised areas and recessed areas such that one row of staple apertures (51) may be higher or lower than another row of staple apertures (51). In other words, in some versions staple deck (348) of cartridge (337) could be modified so that staple deck (348) defines more than one plane and staple apertures (351) are not all along the same plane, but instead are found of different planes that face anvil (318).

Figure 12:
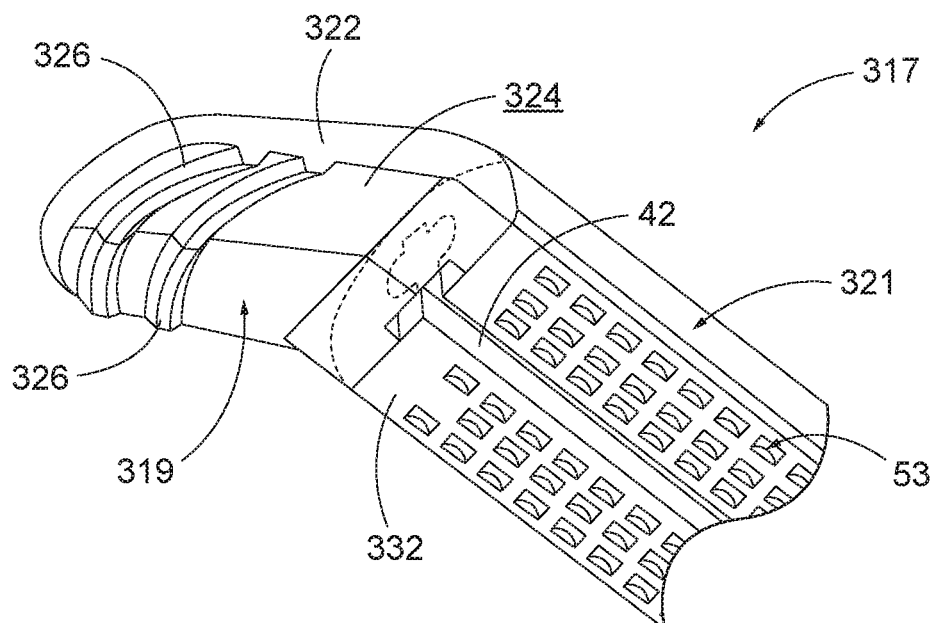
FIG. 12 depicts a partial perspective view of a distal portion of another exemplary anvil for use with the end effector of FIG. 11 and similar to the anvil of FIG. 11, but having an alternate underside surface and shown with a portion of the anvil tip in phantom to reveal the connection between the anvil tip and a body of the anvil.

Returning now to anvil (318), FIG. 11 illustrates anvil body (320) as having recessed areas (328) along an outer region of anvil body (320). With this configuration, anvil body (320) has a raised area (330) along a center region of anvil body (320). Still in other versions, as shown in FIG. 12, anvil (317) may comprise anvil body (321) having a flat area (332) along the portion of anvil body (321) having staple forming pockets (53). In other words, in some instances staple forming pockets (53) may be co-planar, yet in other instances staple forming pockets (53) may be located along different planes defined by the undersurface of anvil body (320). It should be noted that the other features of anvils (317, 318) are identical except for the underside surface configuration as described here. In view of the teachings herein, various modifications and other ways to configure anvils (317, 318) will be apparent to those of ordinary skill in the art.

Figure 13:
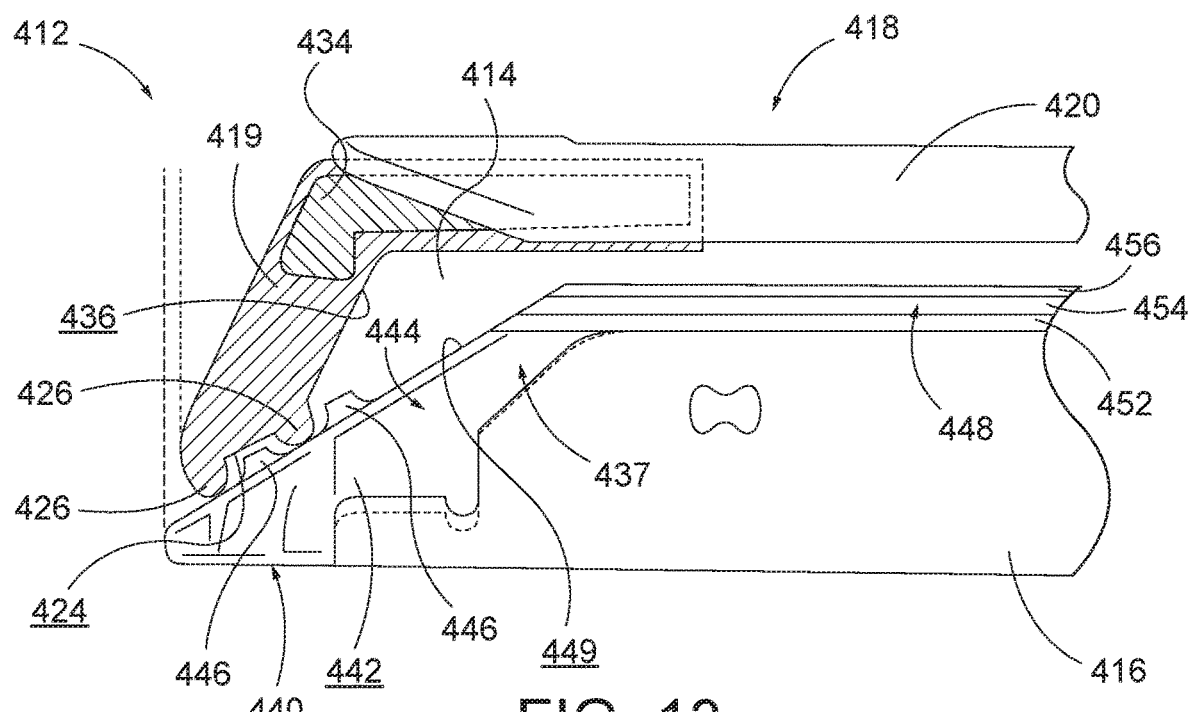
FIG. 13 depicts an enlarged side view of a distal portion of an alternative version of an end effector, with a curved anvil tip and cartridge nose having cooperating features, and shown with the anvil in partial cross section to reveal the connection between the anvil tip and a body of the anvil.

FIG. 13 illustrates another exemplary end effector (412) comprising anvil (418) and lower jaw (416). It will be appreciated that end effector (412) may be used in place of end effector (12) of instrument (10). End effector (412) may be integrally formed with instrument (10) or in the alternative may be interchangeable with end effector (12) of instrument (10). Anvil (418) is operable to pivot relative to lower jaw (416). Anvil (418) and lower jaw (416) may clamp tissue (90) similarly to clamping performed by anvil (18) and lower jaw (16) shown in FIG. 1. End effector (412) further comprises a cartridge (437) that is operable to be placed in lower jaw (416) similarly to cartridge (37) shown in FIG. 3.

Anvil (418) is similar to anvil (318) described above. Anvil (418) comprises an anvil body (420) and an anvil tip (419). Anvil (418) has an elongated shape where anvil body (420) is straight and anvil tip (419) extends distally in an angled or curved manner toward cartridge (437). By way of example, anvil tip (419) is shaped similar to an inverted ski tip. This may provide easier insertion of end effector (412) into a surgical site. For instance, the gentle slope or inverted ski tip shape of anvil tip (419) may provide an atraumatic tissue deflection surface as anvil (418) contacts or moves through tissue. Once placed into a surgical site, the angled shape of anvil tip (419) may provide better maneuverability of end effector (412). Other suitable variations of anvil (418) will be apparent to one of ordinary skill in the art in view of the teachings herein.

Anvil (418) further comprises staple forming pockets (not shown) as described above, and a longitudinal anvil slot (42) as also described above. In the present example, anvil tip (419) is configured as a modular releasable component that selectively connects with or attaches to anvil body (420). In the present example, anvil tip (419) comprises a fastener (434) such as an insert, shim, or other structure that extends proximally and is configured to be received within a distal end of longitudinal slot (42). Some exemplary structures and ways to connect a modular releasable anvil tip with an anvil body are shown and described in U.S. patent application Ser. No. 15/435,607 entitled "Surgical Stapler with Insertable Distal Anvil Tip," filed on Feb. 27, 2017, issued as U.S. Pat. No. 10,729,434 on Aug. 4, 2020, and the disclosure of which is incorporated by reference herein. Still yet, other ways to connect anvil tip (419) with anvil body (420) will be apparent to those of ordinary skill in the art in view of the teachings herein.

Anvil tip (419) comprises a bottom surface (424) that faces cartridge (437) and that is configured to contact tissue (90) when end effector (412) is in a loaded state clamping tissue (90). Along bottom surface (424), anvil tip (419) comprises one or more features (426) that are configured to also contact tissue (90) when end effector (412) is in a loaded state. In the present example, one or more features (426) comprise a pair of raised ribs that generally extend transversely across a width of anvil tip (419). In this manner, the raised ribs protrude or extend from bottom surface (424) toward cartridge (437). While the present example shows two such ribs, in other versions anvil tip (419) comprises greater or fewer ribs. Also, in the present example, one or more features (426) are positioned along or closer to a distal end of anvil tip (419) rather than along a proximal end of anvil tip (419). In particular, in the illustrated version, the pair of raised ribs are configured such that anvil tip (419) distally terminates at one of the pair of raised ribs. In other words, one of the one or more features (426) is located at the distal end of anvil tip (419), with the other one of the one or more features (426) being proximal thereof as shown in FIG. 13. In some other versions, however, one or more features (426) can be located along a middle portion, proximal end, or other portions of bottom surface (424) of anvil tip (419).

In the illustrated version of FIG. 13, anvil tip (419) comprises a steeper angle or greater amount of curvature compared to anvil tip (319). In this manner, a longitudinal axis defined by anvil body (420), and a longitudinal axis defined by a distal portion of anvil tip (419) intersect to form an angle of between about 110 degrees and about 125 degrees. The same angle with anvil tip (319) and body (320) is greater as the angle of anvil tip (319) relative to anvil body (320) is more gradual. For instance the same angle for anvil tip (319) and anvil body (320) in one version is between about 135 degrees and about 160 degrees. Still with either anvil tip (319, 419), these angles may be larger or smaller as those of ordinary skill in the art will understand in view of the teachings herein.

Anvil tip (419) is comprised of an elastomeric material in the present example. With such a construction, in use during clamping tissue anvil tip (419) may deflect or bend from a curved state to a straight or less curved state By way of example only, tip (419) may be deflectable between about 20 degrees and about 70 degrees in a downward direction from a longitudinal axis toward cartridge; between about 0 degrees and about 90 degrees in an upward direction from a longitudinal axis toward cartridge (437). The degree of deflection may be influenced by the thickness and/or density of the tissue that is being compressed between anvil (418) and cartridge (437). In addition, or in the alternative, anvil tip (319) may deflect or bend from a curved state to a straight or less curved state in accordance with at least some of the teachings in U.S. patent application Ser. No. 15/435,573, entitled "Surgical Stapler with Elastically Deformable Tip," filed on Feb. 17, 2017, published as U.S. Pub. No. 2018/0235609 on Aug. 23, 2018, the disclosure of which is incorporated by reference herein. As described above, in this manner anvil tip (419) is operably configured for use in procedures where marching is used. Furthermore, one or more features (426) are similarly formed of an elastomeric material such that they are also elastically deformable. In some versions, one or more features (426) are elastically deformable to a different extent than anvil tip (419) generally. However, in other versions, one or more features (426) can be elastically deformable to the same or to a greater extent compared to anvil tip (419) generally. In view of the teachings herein, various ways to modify and manipulate the degree or extent of elastic deformability of one or more features (426) and/or anvil tip (419) generally will be apparent to those of ordinary skill in the art. Still in other versions, anvil tip (419) and/or its one or more features (426) are not required to be elastically deformable and thus may be rigid.

Cartridge (437) is operable to hold staples similar to staples (47) shown in FIG. 4A for driving into tissue. In the present example, cartridge (437) comprises a nose portion (444) at a distal end. Cartridge nose (444) has a triangular profile. In particular, cartridge nose (444) comprises an upper tapered surface (439), a bottom surface (440), and side surfaces (442). In the present example, bottom surface (440) is generally parallel with a longitudinal axis defined by cartridge (437). In some other examples, bottom surface (440) is angled toward the longitudinal axis defined by cartridge (437), similar to the configuration shown above with respect to cartridge (237).

Along upper surface (439), cartridge (437) comprises one or more features (446) that are configured to also contact tissue (90) when end effector (412) is in a loaded state. In the present example, one or more features (446) comprise a pair of raised ribs that generally extend transversely across a width of cartridge (437). In this manner, the raised ribs protrude or extend from upper surface (439) toward anvil tip (419). While the present example shows two such ribs, in other versions nose portion (444) of cartridge (437) comprises greater or fewer ribs. Also, in the present example, one or more features (446) are positioned along or closer to a middle and distal end of nose portion (444) rather than along a proximal end of nose portion (444). In some other versions, however, one or more features (446) can be located along a proximal end, or other portions of, upper surface (439) of cartridge (437).

In the present version, cartridge (437) and one or more features (446) protruding from nose portion (444) are rigid such that they do not elastically deform when end effector (412) is in a loaded state clamping tissue (90). Furthermore, when end effector (412) is closed and in a non-loaded state not clamping tissue, one or more features (446) of cartridge (437) are configured to complement one or more features (426) of anvil tip (419). In this manner, when tissue (90) is not present within end effector (412), one or more features (446) of cartridge (437) and one or more features (426) of anvil tip (419) cooperate to form a nesting arrangement. In this nesting arrangement, one or more features (426) of anvil tip (419) are positionable adjacent to one or more features (446) of cartridge (437). In the illustrated version of FIG. 13, when nested, a distal-most rib of anvil tip (419) is positioned adjacent to and distal to a distal-most rib of cartridge (437). In other versions where a nesting arrangement exists, a distal-most rib of anvil tip (419) can be positioned adjacent to and proximal to a distal-most rib of cartridge (437), similar to end effector (312) described above.

With the arrangement described above and as illustrated in FIG. 13, end effector (412) comprises the combination of elastically deformable anvil tip (419) having one or more features (426), combined with rigid cartridge nose (444) having one or more features (446). Furthermore, as described above the one or more features (426) cooperate with, or are complementary to, the one or more features (446). In other versions, one or more features (446) of cartridge nose (444) can be configured as elastically deformable while one or more features (426) of anvil tip (419) can be configured as rigid. Still yet in other versions, both of one or more features (426, 446) can be elastically deformable, or both can be rigid.

With end effector (412), bottom surface (424) of anvil tip (419) and upper surface (439) of cartridge nose portion (444) are generally parallel surfaces. This parallel orientation promotes equal nesting of one or more features (426) of anvil (419) with one or more features (446) of nose portion (444). For instance, in the present example, the most distal features (426, 446) will nest to the same extent or degree as the most proximal features (326, 446). In view of the teachings herein, other arrangements for the orientation of bottom surface (424) and upper surface (439), including non-parallel arrangements, will be apparent to those of ordinary skill in the art.

Anvil tip (419) has a steep angle as described above. With this configuration, anvil tip (419) comprises a rear surface (436) that extends along the distal portion of anvil tip (419) that defines the longitudinal axis of anvil tip (419) as described above. With the steep angle of anvil tip (419), rear surface (436) is not parallel with upper surface (439) of cartridge (437). Thus, end effector (412) comprises a void space (414) between anvil tip (419) and upper surface (439) of cartridge (437). In the present example, when end effector (412) is closed in a non-loaded state where tissue is not clamped between anvil (419) and cartridge (437), void space (414) has a triangular profile.

While the present example of FIG. 13 is described as one or more features (426) of anvil tip (419) and one or more features (446) of cartridge nose (444) adopting a nesting arrangement, in some instances such an arrangement may be a contacting arrangement where one or more features (426) of anvil tip (419) contact with upper surface (439) of cartridge nose (444) when end effector (412) is closed and in an unloaded state and/or one or more features (446) of cartridge nose (444) contact with bottom surface (424) of anvil tip (419) when end effector (412) is closed and in an unloaded state. In such a nested and contacting configuration, the gap between the flat regions of bottom surface (424) and upper surface (439) generally equals the distance the protruding ribs extend away from their respective bottom surface (424) and upper surface (439). Some other nesting arrangements are non-contacting arrangements where, even when end effector (412) is closed and in an unloaded state where no tissue is within end effector (412), one or more features (426) of anvil tip (419) do not contact cartridge (437); and similarly one or more features (446) of cartridge nose (444) do not contact anvil tip (419). In a loaded state, regardless if the nesting arrangement is contacting or non-contacting, one or more features (426, 446) contact tissue in a manner that applies staggered concentrations of force to clamped tissue (90). These staggered concentrations of force coincide with the locations where one or more features (426, 446) that protrude from respective anvil tip (419) and cartridge nose (444) contact tissue (90).

In instances when anvil tip (419) and cartridge nose (444) have a contacting arrangement, in marching applications when tissue (90) is clamped between a closed cartridge (437) and anvil (418), a user would be able to determine whether they are at the final cut and staple location along the tissue since at that point the one or more features (426, 446) would engage in their nested arrangement. This could be detected by the user visually and/or based on tactile feedback from prior cut and staple iterations. In other applications where an entire tissue portion or vessel is supposed to be captured between a closed cartridge (437) and anvil (418), such confirmation and feedback can be provided in this manner as well. Furthermore, where a contacting nesting arrangement is used for anvil tip (419) and cartridge nose (444), the one or more features (426, 446) also provide a tissue stop or locking feature that prevents tissue (90) that is clamped between anvil (418) and cartridge (437) from spilling over the end of end effector (412).

It will be appreciated that in some instances, end effector (412) may be rotated before, during, or after clamping tissue (90). As a result, the curved shape of anvil (418) may also provide more accessible viewing of anvil tip (419) or regions substantially adjacent anvil tip (419). The curve of anvil (418) may further promote easy insertion of end effector (412) into tissue in an atraumatic manner. Furthermore, it may be easier to fit end effector (412) through a trocar or other devices operable to introduce end effector (412) into a surgical site due to the curve of anvil (418) of end effector (412).

Referring again to FIG. 13, cartridge (437) comprises vertical slot (not shown) having the same or similar structure and function as vertical slot (49) discussed above. Cartridge (437) also comprises staple apertures (not shown) having the same or similar structure and function as staple apertures (51) discussed above. In the present example, cartridge (437) comprises a stepped staple deck (448). Stepped staple deck (448) includes regions or areas of staple deck (448) that define different planes of staple deck (448) such that staple apertures along staple deck (448) may be located along different planes that face anvil (418). In this manner, cartridge (437) may be fitted with staples of varying lengths. For instance an outer row of staples may be longer compared to the staples used closer to a centerline of cartridge (437). This may promote better stapling of tissue having a thickness that varies across the width of end effector (412).

In the present example of FIG. 13, cartridge (437) comprises stepped staple deck (448) that defines three separate planes. A first plane is defined by an outer region (452) of staple deck (448). The first plane and outer region (452) are common to both sides of staple deck (448) such that the outer region on one side of staple deck (448) is co-planar with the outer region on the other side of staple deck (448). A second plane is defined by a middle region (454) of staple deck (448). The second plane and middle region (454) are common to both sides of staple deck (448) such that the middle region on one side of staple deck (448) is co-planar with the middle region on the other side of staple deck (448). A third plane is defined by an inner region (456) of staple deck (448). The third plane and inner region (456) are common to both sides of staple deck (448) such that the inner region on one side of staple deck (448) is co-planar with the inner region on the other side of staple deck (448).

Along the centerline of staple deck (448), vertical slot (not shown) divides the two sides of staple deck (448). With the above described configuration, each side of staple deck (448) is a mirror image of the other, although such a configuration is not required in all versions. In view of the teachings herein, those of ordinary skill in the art will understand the various ways to configure outer region (452), middle region (454), and inner region (456) of staple deck (448) relative to one another, along with the various sized staples that may be used in each region. Various other modifications and other ways to configure cartridge (437) will be apparent to those of ordinary skill in the art. For instance, cartridge (437) may be modified similar to cartridge (337) above by having cartridge (437) include a staple deck that defines a single plane such that all staple apertures are located along the same plane facing anvil (418).

Returning now to anvil (418), anvil body (420) may have recessed areas along an outer region of anvil body (420) as described above with respect to anvil body (320). In other versions, anvil (418) may comprise anvil body (420) having a flat area along the portion of anvil body (420) having staple forming pockets as described above with respect to anvil body (321) of FIG. 12. In view of the teachings herein, various modifications and other ways to configure anvil (418) will be apparent to those of ordinary skill in the art. For instance, where a stepped staple deck is used, anvil body (420) may have a complementary stepped underside surface to maintain a consistent gap between anvil (418) and cartridge (437) when end effector (412) is closed. In other versions, anvil body (420) may be stepped or not stepped such that a consistent gap is not required across the lateral width of anvil (418) and cartridge (437).

As also shown in FIG. 13, end effector (412) is configured such that nose (444) of cartridge (437) extends distal to anvil tip (419) when end effector (412) is closed in a non-loaded state. In use, with elastically deformable anvil tip (419), anvil tip (419) may deflect when contacting or clamping tissue. In its deflected state, anvil tip (419) may extend distally such that anvil tip (419) aligns with the distal end of nose (444) of cartridge (437), or in some versions extends distally past the distal end of nose (444).

Figure 14:
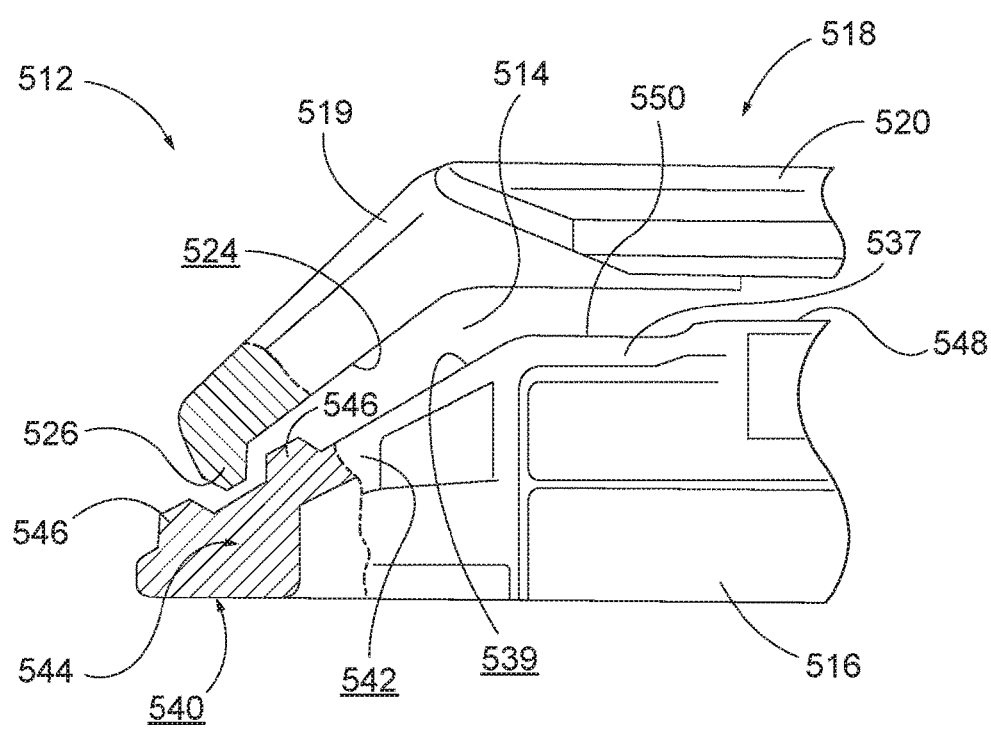
FIG. 14 depicts an enlarged side view of a distal portion of an alternative version of an end effector, with a curved anvil tip and cartridge nose having cooperating features, and shown with a portion of the anvil tip and cartridge nose in cross section.

FIG. 14 illustrates another exemplary end effector (512) comprising anvil (518) and lower jaw (516). It will be appreciated that end effector (512) may be used in place of end effector (12) of instrument (10). End effector (512) may be integrally formed with instrument (10) or in the alternative may be interchangeable with end effector (12) of instrument (10). Anvil (518) is operable to pivot relative to lower jaw (516). Anvil (518) and lower jaw (516) may clamp tissue (90) similarly to clamping performed by anvil (18) and lower jaw (16) shown in FIG. 1. End effector (512) further comprises a cartridge (537) that is operable to be placed in lower jaw (516) similarly to cartridge (37) shown in FIG. 3.

Anvil (518) is similar to anvils (318, 418) described above. Anvil (518) comprises an anvil body (520) and an anvil tip (519). Anvil (518) has an elongated shape where anvil body (520) is straight and anvil tip (519) extends distally in an angled or curved manner toward cartridge (537). By way of example, anvil tip (519) is shaped similar to an inverted ski tip. This may provide easier insertion of end effector (512) into a surgical site. For instance, the gentle slope or inverted ski tip shape of anvil tip (519) may provide an atraumatic tissue deflection surface as anvil (518) contacts or moves through tissue. Once placed into a surgical site, the angled shape of anvil tip (519) may provide better maneuverability of end effector (512). Other suitable variations of anvil (518) will be apparent to one of ordinary skill in the art in view of the teachings herein.

Anvil (518) further comprises staple forming pockets (not shown) as described above, and a longitudinal anvil slot (not shown) as also described above. In the present example, anvil tip (519) is configured as a modular releasable component that selectively connects with or attaches to anvil body (520). In the present example, anvil tip (519) comprises a fastener (not shown) such as an insert, shim, or other structure that extends proximally and is configured to be received within a distal end of the longitudinal slot. Some exemplary structures and ways to connect a modular releasable anvil tip with an anvil body are shown and described in U.S. patent application Ser. No. 15/435,607 entitled "Surgical Stapler with Insertable Distal Anvil Tip," filed on Feb. 17, 2017, issued as U.S. Pat. No. 10,729,434 on Aug. 4, 2020, and the disclosure of which is incorporated by reference herein. Still yet, other ways to connect anvil tip (519) with anvil body (520) will be apparent to those of ordinary skill in the art in view of the teachings herein.

Anvil tip (519) comprises a bottom surface (524) that faces cartridge (537) and that is configured to contact tissue (90) when end effector (512) is in a loaded state clamping tissue (90). Along bottom surface (524), anvil tip (519) comprises one or more features (526) that are configured to also contact tissue (90) when end effector (512) is in a loaded state. In the present example, one or more features (526) comprise a single raised rib that generally extends transversely across a width of anvil tip (519). In this manner, the raised rib protrudes or extends from bottom surface (524) toward cartridge (537). While the present example shows only a single rib, in other versions anvil tip (519) comprises greater or fewer ribs. Also, in the present example, one or more features (526) are positioned along a distal end of anvil tip (519) rather than along a more proximal portion of anvil tip (519). In particular, in the illustrated version, the rib is configured such that anvil tip (519) distally terminates at the rib. In some other versions, however, one or more features (526) are not required to be at the distal end of anvil tip (519), and can instead or in addition be located along a more proximal portion of bottom surface (524) of anvil tip (519).

In the illustrated version of FIG. 14, anvil tip (519) comprises a steeper angle or greater amount of curvature compared to anvil tip (319), but less than that compared to anvil tip (419). In this manner, a longitudinal axis defined by anvil body (520), and a longitudinal axis defined by a distal portion of anvil tip (519) intersect to form an angle of between about 130 degrees and about 150 degrees. The same angle with anvil tip (319) and body (320) is greater as the angle of anvil tip (319) relative to anvil body (320) is more gradual. The same angle with anvil tip (419) and body (420) is less as the angle of anvil tip (419) relative to anvil body (420) is steeper. Still with any of these anvil tips (319, 419, 519) these angles may be larger or smaller as those of ordinary skill in the art will understand in view of the teachings herein.

Anvil tip (519) is comprised of an elastomeric material in the present example. With such a construction, in use during clamping tissue anvil tip (519) may deflect or bend from a curved state to a straight or less curved state. By way of example only, tip (519) may be deflectable between about 20 degrees and about 70 degrees in a downward direction from a longitudinal axis toward cartridge; between about 0 degrees and about 90 degrees in an upward direction from a longitudinal axis toward cartridge (537). The degree of deflection may be influenced by the thickness and/or density of the tissue that is being compressed between anvil (518) and cartridge (537). In addition, or in the alternative, anvil tip (319) may deflect or bend from a curved state to a straight or less curved state in accordance with at least some of the teachings in U.S. patent application Ser. No. 15/435,573, entitled "Surgical Stapler with Elastically Deformable Tip," filed on Feb. 17, 2017, published as U.S. Pub. No. 2018/

0235609 on Aug. 23, 2018, the disclosure of which is incorporated by reference herein. As described above, in this manner anvil tip (519) is operably configured for use in procedures where marching is used. Furthermore, one or more features (526) are similarly formed of an elastomeric material such that they are also elastically deformable. In some versions, one or more features (526) are elastically deformable to a different extent than anvil tip (519) generally. However, in other versions, one or more features (526) can be elastically deformable to the same or to a greater extent compared to anvil tip (519) generally. In view of the teachings herein, various ways to modify and manipulate the degree or extent of elastic deformability of one or more features (526) and/or anvil tip (519) generally will be apparent to those of ordinary skill in the art. Still in other versions, anvil tip (519) and/or its one or more features (526) are not required to be elastically deformable and thus may be rigid.

Cartridge (537) is operable to hold staples similar to staples (47) shown in FIG. 4A for driving into tissue. In the present example, cartridge (537) comprises a nose portion (544) at a distal end. Cartridge nose (544) has a triangular profile. In particular, cartridge nose (544) comprises an upper tapered surface (539), a bottom surface (540), and side surfaces (542). In the present example, bottom surface (540) is generally parallel with a longitudinal axis defined by cartridge (537). In some other examples, bottom surface (540) is angled toward the longitudinal axis defined by cartridge (537), similar to the configuration shown above with respect to cartridge (237).

Along upper surface (539), cartridge (537) comprises one or more features (546) that are configured to also contact tissue (90) when end effector (512) is in a loaded state. In the present example, one or more features (546) comprise a pair of raised ribs that generally extend transversely across a width of cartridge (537). In this manner, the raised ribs protrude or extend from upper surface (539) toward anvil tip (519). While the present example shows two such ribs, in other versions nose portion (544) of cartridge (537) comprises greater or fewer ribs. Also, in the present example, one or more features (546) are positioned along or closer to a middle and distal end of nose portion (544) rather than along a proximal end of nose portion (544). In some other versions, however, one or more features (546) can be located along a proximal end, or other portions of upper surface (539) of cartridge (537).

In the present version, cartridge (537) and one or more features (546) protruding from nose portion (544) are rigid such that they do not elastically deform when end effector (512) is in a loaded state clamping tissue (90). Furthermore, when end effector (512) is closed and in a non-loaded state not clamping tissue, one or more features (546) of cartridge (537) are configured to complement one or more features (526) of anvil tip (519). In this manner, when tissue (90) is not present within end effector (512), one or more features (546) of cartridge (537) and one or more features (526) of anvil tip (519) cooperate to form a nesting arrangement. In this nesting arrangement, one or more features (526) of anvil tip (519) are positionable adjacent to one or more features (546) of cartridge (537). In the illustrated version of FIG. 14, when nested, the single distal rib of anvil tip (519) is positioned in alignment between two ribs of cartridge (537). In other versions where a nesting arrangement exists, the single distal rib of anvil tip (519) can be positioned proximal or distal the two ribs of cartridge (537).

With the arrangement described above and as illustrated in FIG. 14, end effector (512) comprises the combination of elastically deformable anvil tip (519) having one or more features (526) combined with rigid cartridge nose (544) having one or more features (546). Furthermore, as described above the one or more features (526) cooperate with, or are complementary to, the one or more features (546). In other versions, one or more features (546) of cartridge nose (544) can be configured as elastically deformable while one or more features (526) of anvil tip (519) can be configured as rigid. Still yet in other versions, both of one or more features (526, 546) can be elastically deformable, or both can be rigid.

With end effector (512), bottom surface (524) of anvil tip (519) and upper surface (539) of cartridge nose portion (544) are angled to different degrees such that surfaces (524, 539) are not parallel. Thus, end effector (512) comprises a void space (514) between anvil tip (519) and upper surface (539) of cartridge (537). In the present example, when end effector (512) is closed in a non-loaded state where tissue is not clamped between anvil (519) and cartridge (537), void space (514) has a triangular profile. In view of the teachings herein, other arrangements for the orientation of bottom surface (524) and upper surface (539), including parallel arrangements, will be apparent to those of ordinary skill in the art.

While the present example of FIG. 14 is described as one or more features (526) of anvil tip (519) and one or more features (546) of cartridge nose (544) adopting a nesting arrangement, in the illustrated version such an arrangement is a non-contacting arrangement where even when end effector (512) is closed and in an unloaded state where no tissue is within end effector (512), one or more features (526) of anvil tip (519) do not contact cartridge (537); and similarly one or more features (546) of cartridge nose (544) do not contact anvil tip (519). In some other versions, end effector (512) may have a nesting arrangement that is a contacting arrangement where one or more features (526) of anvil tip (519) contact with upper surface (539) of cartridge nose (544) when end effector (512) is closed and in an unloaded state and/or one or more features (546) of cartridge nose (544) contact with bottom surface (524) of anvil tip (519) when end effector (512) is closed and in an unloaded state. In a loaded state, regardless if the nesting arrangement is contacting or non-contacting, one or more features (526, 546) contact tissue in a manner that applies staggered concentrations of force to clamped tissue (90). These staggered concentrations of force coincide with the locations where one or more features (526, 546) that protrude from respective anvil tip (519) and cartridge nose (544) contact tissue (90).

In instances when anvil tip (519) and cartridge nose (544) have a non-contacting arrangement, in marching applications when tissue (90) is clamped between a closed cartridge (537) and anvil (518), a user would be able to determine whether they are at the final cut and staple location along the tissue since at that point the one or more features (526, 546) would be located in proximity to each other in their nested arrangement. This could be detected by the user visually. In other applications where an entire tissue portion or vessel is supposed to be captured between a closed cartridge (537) and anvil (518), such confirmation can be provided in this manner as well. Furthermore, even in a non-contacting nesting arrangement, one or more features (526, 546) also provide a tissue stop or locking feature that inhibits tissue (90) that is clamped between anvil (518) and cartridge (537) from spilling over the end of end effector (512).

It will be appreciated that in some instances, end effector (512) may be rotated before, during, or after clamping tissue (90). As a result, the curved shape of anvil (518) may also provide more accessible viewing of anvil tip (519) or regions substantially adjacent anvil tip (519). The curve of anvil (518) may further promote easy insertion of end effector (512) into tissue in an atraumatic manner. Furthermore, it may be easier to fit end effector (512) through a trocar or other devices operable to introduce end effector (512) into a surgical site due to the curve of anvil (518) of end effector (512).

Referring again to FIG. 14, cartridge (537) comprises vertical slot (not shown) having the same or similar structure and function as vertical slot (49) discussed above. Cartridge (537) also comprises staple apertures (not shown) having the same or similar structure and function as staple apertures (51) discussed above. In the present example, cartridge (537) is generally flat along a staple deck (548) with staple apertures being along the same plane defined by staple deck (548). Distal to staple deck (548), cartridge (537) comprises shelf (550), which is also flat but is slightly recessed relative to staple deck (548). In view of the teachings herein, various modifications and other ways to configure cartridge (537) will be apparent to those of ordinary skill in the art. For instance, cartridge (537) may be modified similar to cartridge (37) above by having cartridge (537) include separate raised areas and recessed areas such that one row of staple apertures may be higher or lower than another row of staple apertures. In other words, in some versions staple deck (548) of cartridge (537) could be modified so that staple deck (548) defines more than one plane and staple apertures are not all along the same plane, but instead are found of different planes facing anvil (518), the same or similar to that described above for cartridge (437).

Returning now to anvil (518), anvil body (520) may have recessed areas along an outer region of anvil body (520) as described above with respect to anvil body (320). In other versions, anvil (518) may comprise anvil body (520) having a flat area along the portion of anvil body (520) having staple forming pockets as described above with respect to anvil body (321) of FIG. 12. In view of the teachings herein, various modifications and other ways to configure anvil (518) will be apparent to those of ordinary skill in the art. For instance, where a stepped staple deck is used, anvil body (520) may have a complementary stepped underside surface to maintain a consistent gap between anvil (518) and cartridge (537) when end effector (512) is closed. In other versions, anvil body (520) may be stepped or not stepped such that a consistent gap is not required across the lateral width of anvil (518) and cartridge (537).

As also shown in FIG. 14, end effector (512) is configured such that nose (544) of cartridge (537) extends distal to anvil tip (519) when end effector (512) is closed in a non-loaded state. In use, elastically deformable anvil tip (519) may deflect when contacting or clamping tissue. In its deflected state, anvil tip (519) may extend distally such that anvil tip (519) remains proximal to the distal end of cartridge nose (544). In other examples anvil tip (519) may extend when deflected to align with the distal end of nose (544) of cartridge (537). Still in other examples, anvil tip (519) may extend when deflected distally past the distal end of nose (544).

Figure 15:
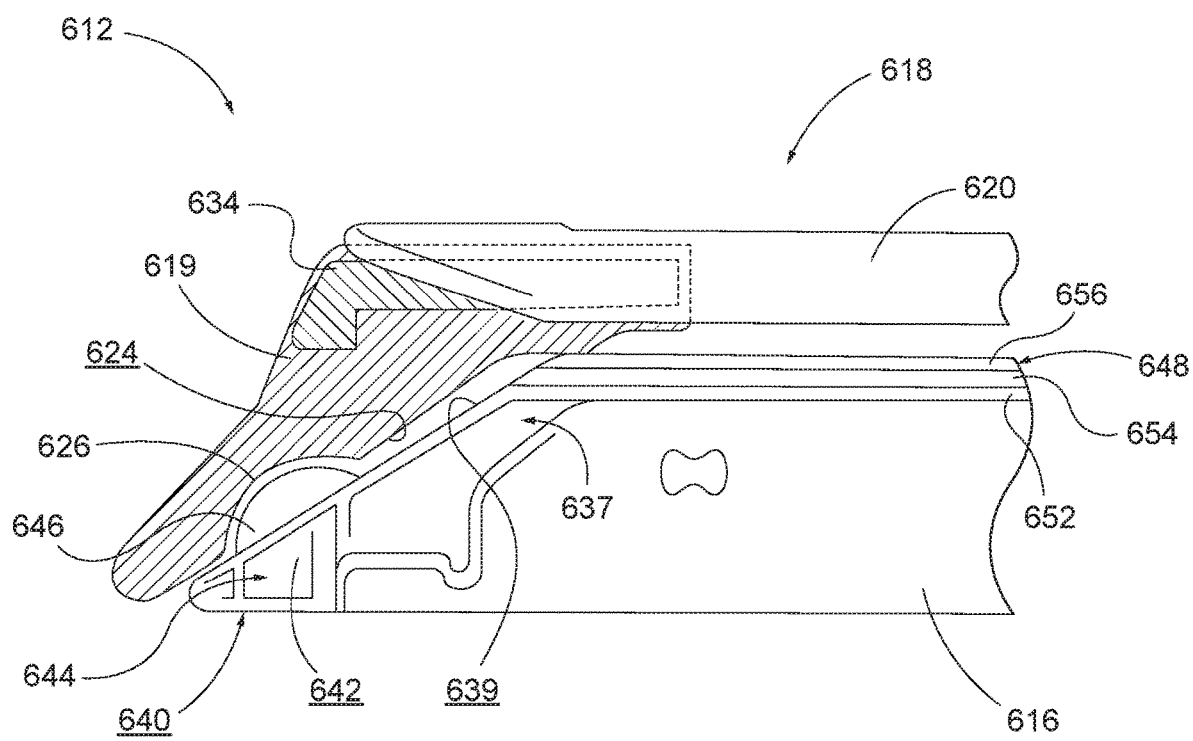
FIG. 15 depicts an enlarged side view of a distal portion of an alternative version of an end effector, with a curved anvil tip and cartridge nose having cooperating features, and shown with the anvil in partial cross section to reveal the connection between the anvil tip and a body of the anvil.

FIG. 15 illustrates another exemplary end effector (612) comprising anvil (618) and lower jaw (616). It will be appreciated that end effector (612) may be used in place of end effector (12) of instrument (10). End effector (612) may be integrally formed with instrument (10) or in the alternative may be interchangeable with end effector (12) of instrument (10). Anvil (618) is operable to pivot relative to lower jaw (616). Anvil (618) and lower jaw (616) may clamp tissue (90) similarly to clamping performed by anvil (18) and lower jaw (16) shown in FIG. 1. End effector (612) further comprises a cartridge (637) that is operable to be placed in lower jaw (616) similarly to cartridge (37) shown in FIG. 3.

Anvil (618) is similar to anvil (418) described above. Anvil (618) comprises an anvil body (620) and an anvil tip (619). Anvil (618) has an elongated shape where anvil body (620) is straight and anvil tip (619) extends distally in an angled or curved manner toward cartridge (637). By way of example, anvil tip (619) is shaped similar to an inverted ski tip. This may provide easier insertion of end effector (612) into a surgical site. For instance, the gentle slope or inverted ski tip shape of anvil tip (619) may provide an atraumatic tissue deflection surface as anvil (618) contacts or moves through tissue. Once placed into a surgical site, the angled shape of anvil tip (619) may provide better maneuverability of end effector (612). Other suitable variations of anvil (618) will be apparent to one of ordinary skill in the art in view of the teachings herein.

Anvil (618) further comprises staple forming pockets (not shown) as described above, and a longitudinal anvil slot (42) as also described above. In the present example, anvil tip (619) is configured as a modular releasable component that selectively connects with or attaches to anvil body (620). In the present example, anvil tip (619) comprises a fastener (634) such as an insert, shim, or other structure that extends proximally and is configured to be received within a distal end of longitudinal slot (42). Some exemplary structures and ways to connect a modular releasable anvil tip with an anvil body are shown and described in U.S. patent application Ser. No. 15/435,607 entitled "Surgical Stapler with Insertable Distal Anvil Tip," filed on Feb. 17, 2017, issued in U.S. Pat. No. 10,729,434 on Aug. 4, 2020, and the disclosure of which is incorporated by reference herein. Still yet, other ways to connect anvil tip (619) with anvil body (620) will be apparent to those of ordinary skill in the art in view of the teachings herein.

Anvil tip (619) comprises a bottom surface (624) that faces cartridge (637) and that is configured to contact tissue (90) when end effector (612) is in a loaded state clamping tissue (90). Along bottom surface (624), anvil tip (619) comprises one or more features (626) that are configured to also contact tissue (90) when end effector (612) is in a loaded state. In the present example, one or more features (626) comprise a recessed area in the form of a circular depression (i.e., a concave spherical dome) in bottom surface (624) of anvil tip (619). While the present example shows a single recessed area in the form of a circular depression, in other versions anvil tip (519) may comprise more than one recessed area that may also have other shapes besides or in addition to a circular depression.

In the illustrated version of FIG. 15, anvil tip (619) comprises a similar angle or similar amount of curvature compared to anvil tip (319). In this manner, a longitudinal axis defined by anvil body (620), and a longitudinal axis defined by a distal portion of anvil tip (619) intersect to form an angle of between about 135 degrees and about 160 degrees. Still with either anvil tip (319, 619) these angles may be larger or smaller as those of ordinary skill in the art will understand in view of the teachings herein.

Anvil tip (619) is comprised of an elastomeric material in the present example. With such a construction, in use during clamping tissue anvil tip (619) may deflect or bend from a curved state to a straight or less curved state. By way of example only, tip (619) may be deflectable between about 20 degrees and about 70 degrees in a downward direction from a longitudinal axis toward cartridge; between about 0 degrees and about 90 degrees in an upward direction from a longitudinal axis toward cartridge (637). The degree of deflection may be influenced by the thickness and/or density of the tissue that is being compressed between anvil (618) and cartridge (637). In addition, or in the alternative, anvil tip (319) may deflect or bend from a curved state to a straight or less curved state in accordance with at least some of the teachings in U.S. patent application Ser. No. 15/435,573, entitled "Surgical Stapler with Elastically Deformable Tip," filed on Feb. 17, 2017, published as U.S. Pub. No. 2018/0235609 on Aug. 23, 2018, the disclosure of which is incorporated by reference herein. As described above, in this manner anvil tip (619) is operably configured for use in procedures where marching is used. In view of the teachings herein, various ways to modify and manipulate the degree or extent of elastic deformability of anvil tip (619) will be apparent to those of ordinary skill in the art. Still in other versions, anvil tip (619) is not required to be elastically deformable and thus may be rigid.

Cartridge (637) is operable to hold staples similar to staples (47) shown in FIG. 4A for driving into tissue. In the present example, cartridge (637) comprises a nose portion (644) at a distal end. Cartridge nose (644) has a triangular profile. In particular, cartridge nose (644) comprises an upper tapered surface (639), a bottom surface (640), and side surfaces (642). In the present example, bottom surface (640) is generally parallel with a longitudinal axis defined by cartridge (637). In some other examples, bottom surface (640) is angled toward the longitudinal axis defined by cartridge (637), similar to the configuration shown above with respect to cartridge (237).

Along upper surface (639), cartridge (637) comprises one or more features (646) that are configured to also contact tissue (90) when end effector (612) is in a loaded state. In the present example, one or more features (646) comprise a raised member in the form of a dome shaped protrusion (i.e., a convex spherical dome). In this manner, the raised member protrudes or extends from upper surface (639) toward anvil tip (619). While the present example shows one such raised member, in other versions nose portion (644) of cartridge (637) may comprise more than one raised member, and the one or more raised members may take the form of a dome shaped protrusion or another shape that will be apparent to those of ordinary skill in the art in view of the teachings herein. While feature (626) is concave in the present example and feature (646) is convex in the present example, it should be understood that this structural relationship may be reversed. In other words, in some variations feature (626) is convex and feature (646) is concave.

In the present version, cartridge (637) and one or more features (646) protruding from nose portion (644) are rigid such that they do not elastically deform when end effector (612) is in a loaded state clamping tissue (90). Furthermore, when end effector (612) is closed and in a non-loaded state not clamping tissue, one or more features (646) of cartridge (637) are configured to complement one or more features (626) of anvil tip (619). In this manner, when tissue (90) is not present within end effector (612), one or more features (646) of cartridge (637) and one or more features (626) of anvil tip (619) cooperate to form a nesting arrangement. In this nesting arrangement, one or more features (626) of anvil tip (619) are positionable adjacent to one or more features (646) of cartridge (637). In the illustrated version of FIG. 15, when nested, the dome shaped protrusion of cartridge nose (644) is posited within the space defined by circular depression of anvil tip (419).

With the arrangement described above and as illustrated in FIG. 15, end effector (612) comprises the combination of elastically deformable anvil tip (619) having one or more features (626) combined with rigid cartridge nose (644) having one or more features (646). Furthermore, as described above the one or more features (626) cooperate with, or are complementary to, the one or more features (646). In other versions, one or more features (646) of cartridge nose (644) can be configured as elastically deformable while one or more features (626) of anvil tip (619) can be configured as rigid. Still yet in other versions, both of one or more features (626, 646) can be elastically deformable, or both can be rigid.

With end effector (612), bottom surface (624) of anvil tip (619) and upper surface (639) of cartridge nose portion (644) are nearly parallel surfaces. This orientation promotes a general close spacing between bottom surface (624) and upper surface (639) when end effector (612) is closed and in a non-loaded state. In view of the teachings herein, other arrangements for the orientation of bottom surface (624) and upper surface (639), including other non-parallel arrangements or parallel arrangements, will be apparent to those of ordinary skill in the art.

While the present example of FIG. 15 is described as one or more features (626) of anvil tip (619) and one or more features (646) of cartridge nose (644) adopting a nesting arrangement, in some instances, such as the illustrated version, this arrangement is a non-contacting arrangement. In a non-contacting arrangement neither anvil tip (619) nor one or more features (626) of anvil tip (619) contacts with upper surface (639) of cartridge nose (644) when end effector (612) is closed and in an unloaded state, and similarly one or more features (646) of cartridge nose (644) do not contact anvil tip (619). In some other examples, the nesting arrangement may be a contacting arrangement where anvil tip (619) and/or one or more features (626) of anvil tip (619) contacts with upper surface (639) of cartridge nose (644) when end effector (612) is closed and in an unloaded state and/or one or more features (646) of cartridge nose (644) contact with bottom surface (624) of anvil tip (619) when end effector (612) is closed and in an unloaded state. In a loaded state, regardless if the nesting arrangement is contacting or non-contacting, one or more features (626, 646) contact tissue in a manner that applies force to clamped tissue (90).

In instances when anvil tip (619) and cartridge nose (644) are used in marching applications, when tissue (90) is clamped between a closed cartridge (637) and anvil (618), a user would be able to determine whether they are at the final cut and staple location along the tissue since at that point the one or more features (626, 646) may adopt their nested arrangement or a partially nested arrangement. In either arrangement, a portion of the dome shaped protrusion would reside within the space of the circular depression. This could be detected by the user visually in a non-contacting arrangement and visually and/or based on tactile feedback from prior cut and staple iterations in a contacting arrangement where dome shaped protrusion contacts circular depression. In other applications where an entire tissue portion or vessel is supposed to be captured between a closed cartridge (637) and anvil (618), such confirmation and feedback can be provided in this manner as well. Furthermore, the one or more features (626, 646) also provide a tissue stop or locking feature that inhibits or restricts tissue (90) that is clamped between anvil (618) and cartridge (637) from spilling over the end of end effector (612).

It will be appreciated that in some instances, end effector (612) may be rotated before, during, or after clamping tissue (90). As a result, the curved shape of anvil (618) may also provide more accessible viewing of anvil tip (619) or regions substantially adjacent anvil tip (619). The curve of anvil (618) may further promote easy insertion of end effector (612) into tissue in an atraumatic manner. Furthermore, it may be easier to fit end effector (612) through a trocar or other devices operable to introduce end effector (612) into a surgical site due to the curve of anvil (618) of end effector (612).

Referring again to FIG. 15, cartridge (637) comprises vertical slot (not shown) having the same or similar structure and function as vertical slot (49) discussed above. Cartridge (637) also comprises staple apertures (not shown) having the same or similar structure and function as staple apertures (51) discussed above. In the present example, cartridge (637) comprises a stepped staple deck (648). Stepped staple deck (648) includes regions or areas of staple deck (648) that define different planes of staple deck (648) such that staple apertures along staple deck (648) may be located along different planes facing anvil (618). In this manner, cartridge (637) may be fitted with staples of varying lengths. For instance an outer row of staples may be longer compared to the staples used closer to a centerline of cartridge (637).

In the present example of FIG. 15, cartridge (637) comprises stepped staple deck (648) that defines three separate planes. A first plane is defined by an outer region (652) of staple deck (648). The first plane and outer region (652) are common to both sides of staple deck (648) such that the outer region on one side of staple deck (648) is co-planar with the outer region on the other side of staple deck (648). A second plane is defined by a middle region (654) of staple deck (648). The second plane and middle region (654) are common to both sides of staple deck (648) such that the middle region on one side of staple deck (648) is co-planar with the middle region on the other side of staple deck (648). A third plane is defined by an inner region (656) of staple deck (648). The third plane and inner region (656) are common to both sides of staple deck (648) such that the inner region on one side of staple deck (648) is co-planar with the inner region on the other side of staple deck (648).

Along the centerline of staple deck (648), vertical slot (not shown) divides the two sides of staple deck (648). With the above described configuration, each side of staple deck (648) is a mirror image of the other, although such a configuration is not required in all versions. In view of the teachings herein, those of ordinary skill in the art will understand the various ways to configure outer region (652), middle region (654), and inner region (656) of staple deck (648) relative to one another, along with the various sized staples that may be used in each region. Various other modifications and other ways to configure cartridge (637) will be apparent to those of ordinary skill in the art. For instance, cartridge (637) may be modified similar to cartridge (337) above by having cartridge (637) include a staple deck that defines a single plane such that all staple apertures are located along the same plane facing anvil (618).

Returning now to anvil (618), anvil body (620) may have recessed areas along an outer region of anvil body (620) as described above with respect to anvil body (320). In other versions, anvil (618) may comprise anvil body (620) having a flat area along the portion of anvil body (620) having staple forming pockets as described above with respect to anvil body (321) of FIG. 12. In view of the teachings herein, various modifications and other ways to configure anvil (618) will be apparent to those of ordinary skill in the art. For instance, where a stepped staple deck is used, anvil body (620) may have a complementary stepped underside surface to maintain a consistent gap between anvil (618) and cartridge (637) when end effector (612) is closed. In other versions, anvil body (620) may be stepped or not stepped such that a consistent gap is not required across the lateral width of anvil (618) and cartridge (637).

As also shown in FIG. 15, end effector (612) is configured such that a distal end of anvil tip (619) extends distal to cartridge nose (644) when end effector (612) is closed in a non-loaded state. In use, with elastically deformable anvil tip (619), anvil tip (619) may deflect when contacting or clamping tissue. In its deflected state, anvil tip (619) may extend further distally such that anvil tip (619) extends further past the distal end of cartridge nose (644) when end effector (612) clamps tissue. In some other versions end effector (612) may be configured such that the distal end of anvil tip (619) aligns with the distal end of cartridge nose (644), or anvil tip (619) may be proximal to the distal end of cartridge nose (644).

Figure 16:
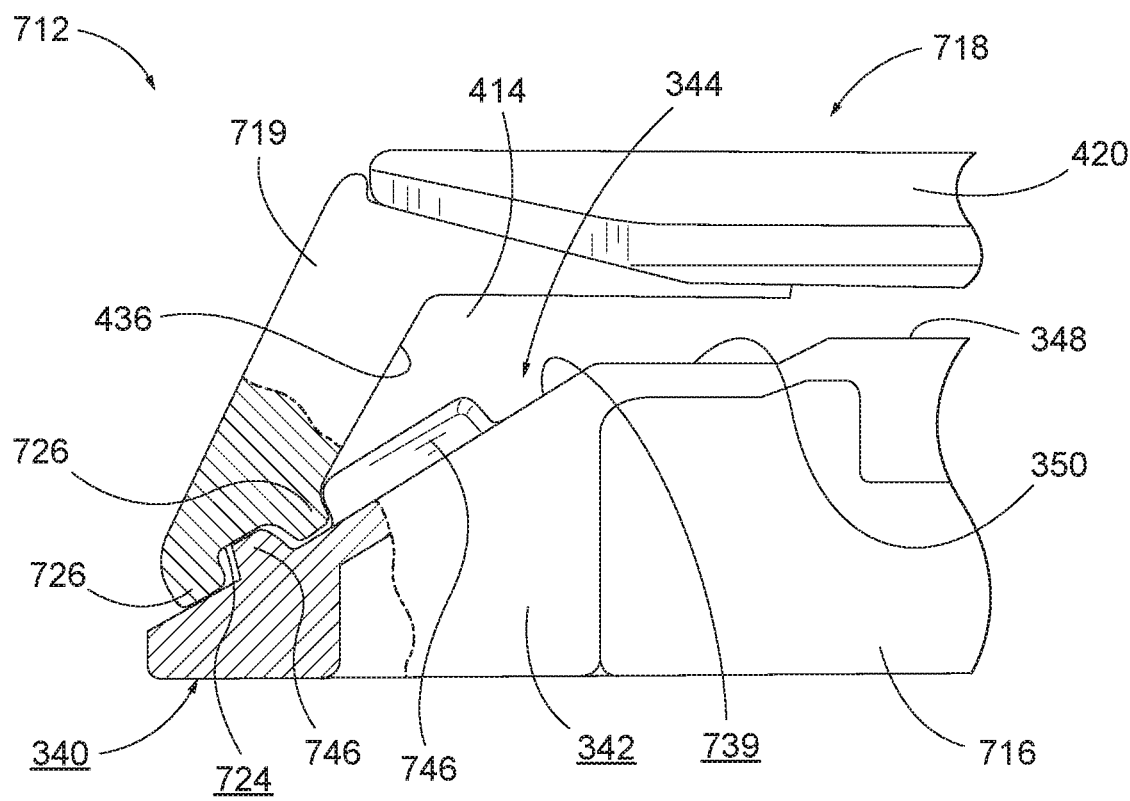
FIG. 16 depicts an enlarged side view of a distal portion of an alternative version of an end effector, with a curved anvil tip and cartridge nose having cooperating features, and shown with a portion of the anvil tip and cartridge nose in cross section.
Figure 17:
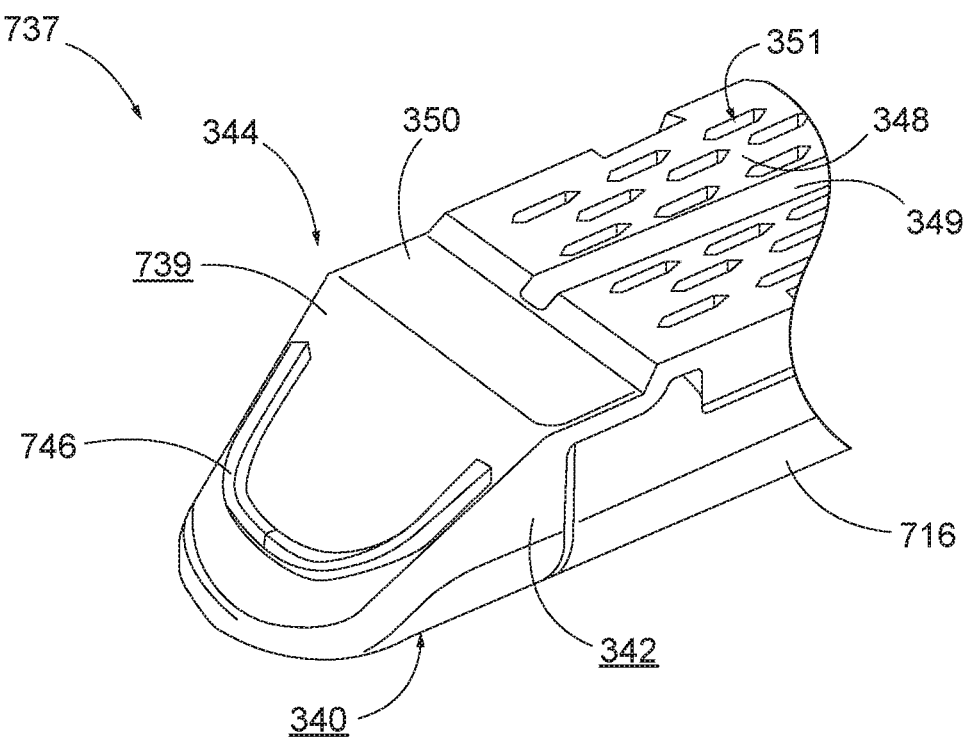
FIG. 17 depicts a partial perspective view of the cartridge nose of FIG. 16.

FIGS. 16 and 17 illustrate another exemplary end effector (712) comprising anvil (718) and lower jaw (716). It will be appreciated that end effector (712) may be used in place of end effector (12) of instrument (10). End effector (712) may be integrally formed with instrument (10) or in the alternative may be interchangeable with end effector (12) of instrument (10). Anvil (718) is operable to pivot relative to lower jaw (716). Anvil (718) and lower jaw (716) may clamp tissue (90) similarly to clamping performed by anvil (18) and lower jaw (16) shown in FIG. 1. End effector (712) further comprises a cartridge (737) that is operable to be placed in lower jaw (716) similarly to cartridge (37) shown in FIG. 3.

Anvil (718) is identical to anvil (418) described above except as noted as follows. Accordingly, the description above of anvil (418) applies equally here to anvil (718), with any differences described below with respect to FIGS. 16 and 17. Additionally, cartridge (737) and lower jaw (716) are identical to cartridge (337) and lower jaw (316) except as noted as follows. Accordingly, the description above of cartridge (337) and lower jaw (316) applies equally here to cartridge (737) and lower jaw (716), with any differences described below with respect to FIGS. 16 and 17.

Along a bottom surface (724), anvil tip (719) comprises one or more features (726) that are configured to also contact tissue (90) when end effector (712) is in a loaded state. In the present example, one or more features (726) comprise a pair of raised ribs that generally extend transversely across a width of anvil tip (719) in a curved arrangement.

Along an upper surface (739), cartridge (737) comprises one or more features (746) configured to also contact tissue (90) when end effector (712) is in a loaded state. In the present example, one or more features (746) comprise a single raised rib having a U-shape or a horseshoe shape or configuration and generally extending transversely across a width of cartridge (737) as shown in FIG. 17.

As described above with other end effectors, when end effector (712) is closed and in a non-loaded state not clamping tissue, one or more features (746) of cartridge (737) are configured to complement one or more features (726) of anvil tip (719). In this manner, when tissue (90) is not present within end effector (712), one or more features (746) of cartridge (737) and one or more features (726) of anvil tip (719) cooperate to form a nesting arrangement. In this nesting arrangement, one or more features (726) of anvil tip (719) are positionable adjacent to one or more features (746) of cartridge (737). In the illustrated version of FIG. 16, when nested, a distal-most rib of anvil tip (719) is positioned adjacent to and distal to the horseshoe shaped rib of cartridge (737), while a proximal-most rib of anvil tip (719) is positioned adjacent to and proximal to the horseshoe shaped rib of cartridge (737). In this manner, the one or more features (726) of anvil (719) surround the one or more features (746) of cartridge (737) with end effector (712) closed and in a non-loaded state. Thus the one or more features (726) of anvil (719) complement the one or more features (746) of cartridge (737) as described above with respect to end effector (412) for example.

As also shown in FIG. 16, end effector (712) is configured such that nose (344) of cartridge (737) extends distal to anvil tip (719) when end effector (712) is closed in a non-loaded state. In use, with elastically deformable anvil tip (719), anvil tip (719) may deflect when contacting or clamping tissue. In its deflected state, anvil tip (719) may extend distally such that anvil tip (719) aligns with the distal end of nose (344) of cartridge (737), or in some versions extends distally past the distal end of nose (344).

Figure 18:
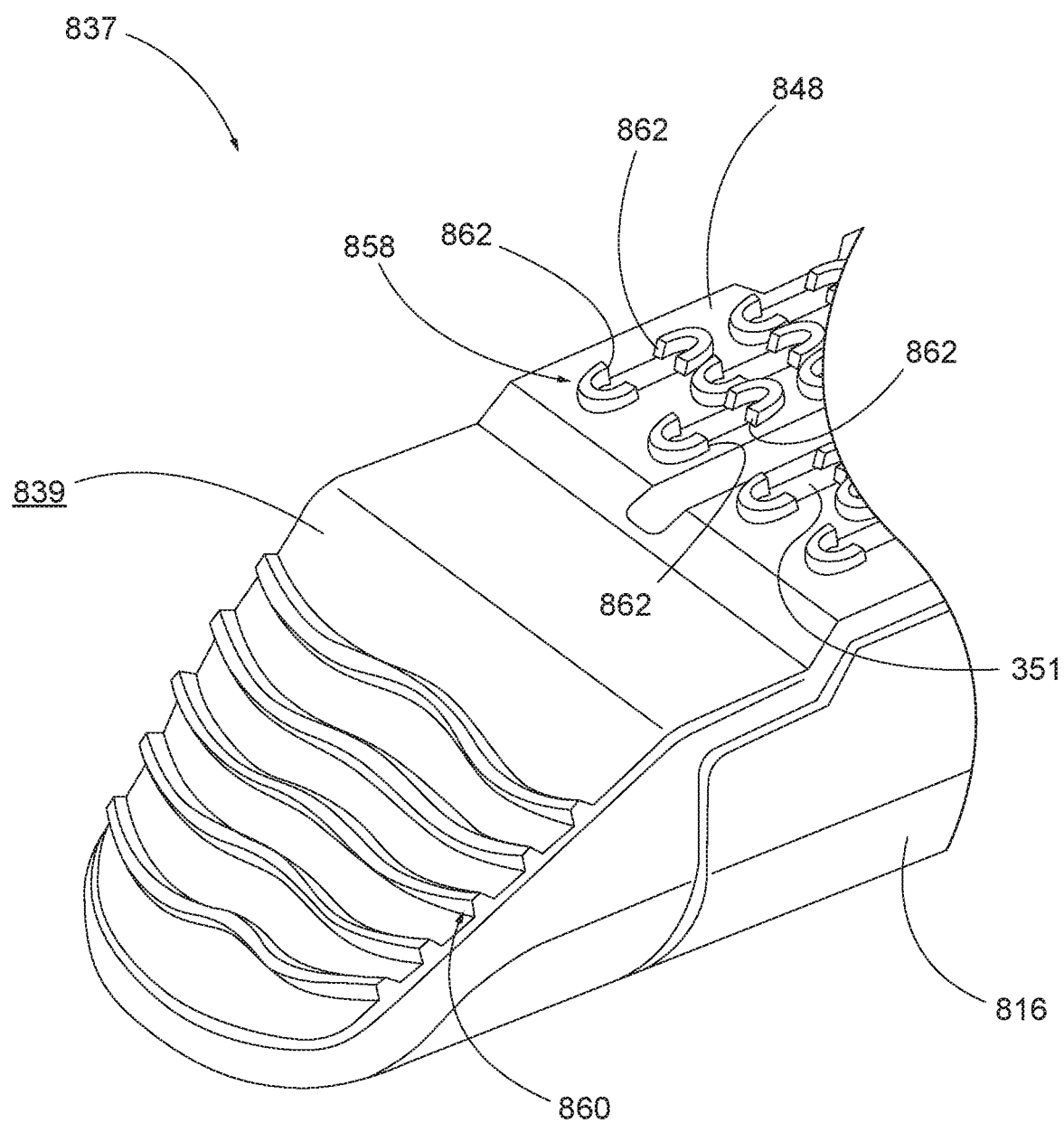
FIG. 18 depicts a partial perspective view of a distal portion of an alternative version of a cartridge for use in an end effector, showing a plurality of gripping features along an angled surface of the cartridge nose and a plurality of gripping features along a deck of the cartridge.

B. Surface Features for Use with Curved and Deformable Anvil Tips and Rigid Cartridge Noses Each with Cooperating Raised Ribs FIG. 18 illustrates a portion of another exemplary cartridge (837) and lower jaw (816) that may be used with any of the end effectors described herein. In this manner, cartridge (837) is compatible with the lower jaws of the end effectors described herein. Cartridge (837) and lower jaw (816) are identical to cartridge (337) and lower jaw (316) except as noted as follows. Accordingly, the description above of cartridge (337) and lower jaw (316) applies equally here to cartridge (837) and lower jaw (816), with any differences described below with respect to FIG. 18.

Cartridge (837) comprises staple deck (848) that includes surface features (858). Surface features (858) are configured to provide enhanced tissue gripping during clamping, cutting, and stapling. In the present example, a pair of surface features (858) are located at opposite ends of each staple forming aperture (351) in staple deck (848). Furthermore, each of surface features (858) comprises a U-shape or horseshoe shape having ends (862) that face each other. Staple forming apertures (351) are arranged in rows where each row's staple forming apertures (351) are offset from staple forming apertures (351) of an adjacent row. With the association of surface features (858) with staple forming apertures (351) as described above, surface features (858) are likewise arranged in rows where each row's surface features (858) are offset from surface features (858) of an adjacent row. With this configuration, surface features (858) are located and configured to provide enhance gripping of tissue at or immediately adjacent to the locations where staples will ultimately pass through tissue to seal or connect cut tissue. In this manner, surface features (858) promote achieving a high quality and successful application of stapling to tissue. In view of the teachings herein, other ways to configure surface features (858) will be apparent to those of ordinary skill in the art.

Cartridge (837) further comprises upper tapered surface (839) that includes surface features (860). Surface features (860) are similar to one or more features (346, 446, 546, 746) described above. In some versions, there may be features on a variation of anvil (18, 218) that are complementary to surface features (860). In such versions, the complementary features cooperate as described above in e.g. end effector (312). In other versions, the anvil used with cartridge (837) may not include features that complement surface features (860).

Surface features (860) are configured to provide enhanced tissue gripping during clamping, cutting, and stapling of tissue. In the present example, surface features (860) are configured as raised ribs having a nested sinusoidal arrangement. While in the present example there are five surface features (860), in other versions the number of surfaces features (860) may be greater or fewer. In view of the teaching herein, other shapes and arrangements for surface features (860) will be apparent to those of ordinary skill in the art.

Both surface features (858) and surface features (860) are rigid in the present example, but in other versions either or both of surface features (858, 860) may be elastically deformable.

In the several examples of end effectors shown and described herein, in at least several examples the anvil of the end effector is the movable jaw portion of the end effector while the cartridge is the fixed or non-movable jaw portion of the end effector. Thus, the modular and elastically deformable anvil tips shown and described herein are attachable or connectable with the movable jaw portion of such end effectors. However, in other versions, modular and elastically deformable tips such as those configurations described herein, can be adapted or modified to be tips for the cartridge or non-movable jaw portion of the end effector. Such modifications to end effectors will be apparent to those of ordinary skill in the art in view of the teachings herein. It should also be understood that, in some variations of instrument (10), the anvil may remain stationary relative to the shaft assembly while the jaw portion holding the staples pivots toward and away from the fixed anvil.

IV. Kits for Anvil Tip and Staple Cartridge Installation, Removal, and Replacement In examples where an instrument with an end effector having an anvil tip and staple cartridge that have cooperating features, it can be useful to provide for a device that aids in installation of the anvil tip to the anvil of the end effector while also simultaneously aiding in the installation of the staple cartridge to the lower jaw of the end effector. Such a device can be useful in marching procedures where replacement staple cartridges are installed sequentially during a cutting and stapling procedure. Such a device can also be helpful to ensure that matching anvil tips and staple cartridges are installed together so the full benefit of the cooperating features of each can be realized.

Figure 19:
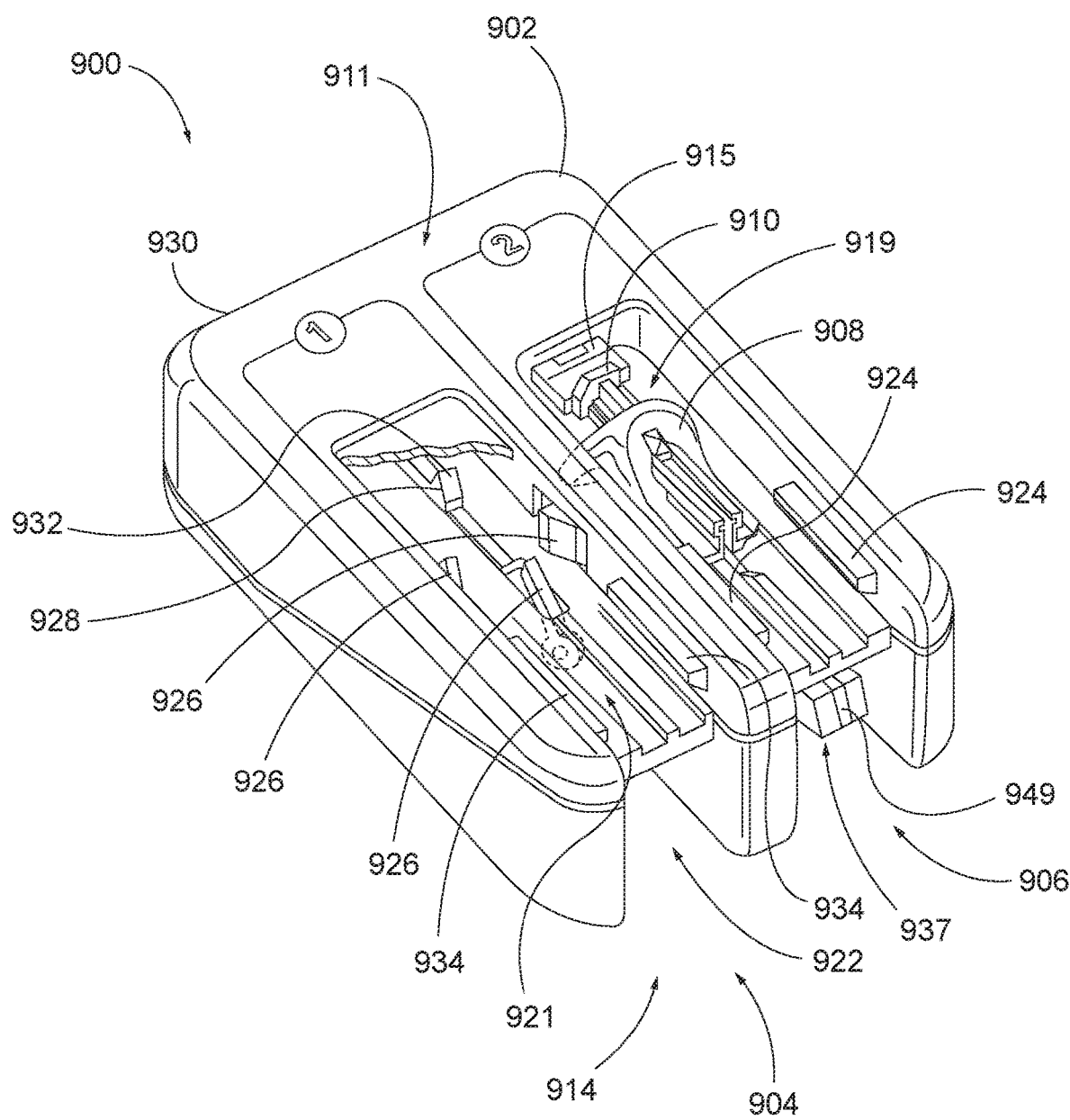
FIG. 19 depicts a perspective view of an exemplary tip replacement cartridge for use with end effectors having detachable anvil tips and cartridges with cooperating features.
Figure 20:
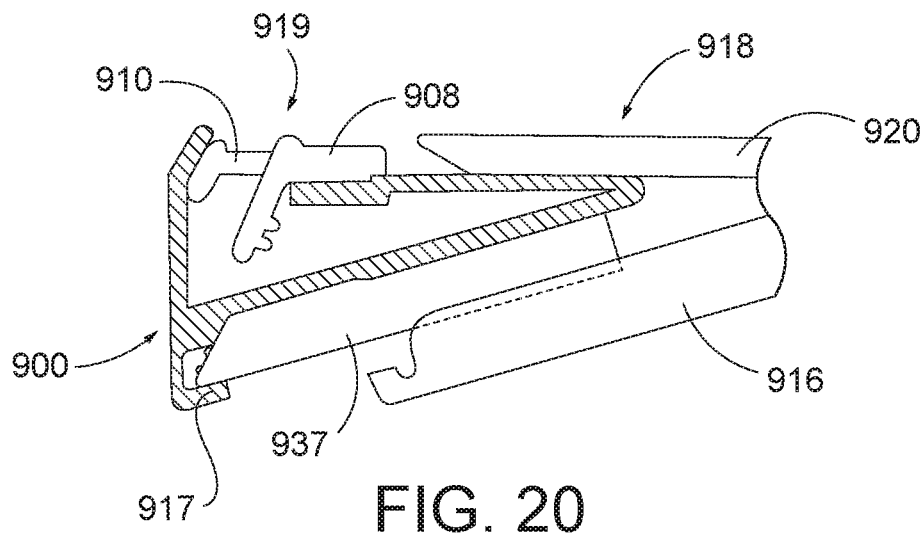
FIG. 20 depicts a first side elevational view in a series of views showing installation of a new anvil tip and cartridge using the tip replacement cartridge of FIG. 19.

FIG. 19 illustrates an exemplary device, in the form of a loading cartridge (900), for installing an anvil tip (919) and a staple cartridge (937) to an end effector (912) of FIG. 20. By way of example, and not limitation, some loading cartridges (900) may be configured for use with end effectors (312, 412, 512, 612, 712) as well as other end effectors that will be apparent to those of ordinary skill in the art in view of the teachings herein. In addition to installing anvil tip (919) and cartridge (937), loading cartridge (900) is further configured to aid in removing a previously installed or existing anvil tip (919) and/or a previously installed or existing staple cartridge (937) from end effector (912). Loading cartridge (900) may be considered as installing a new anvil tip and staple cartridge for a first use of an end effector, or loading cartridge (900) may be considered as installing a replacement anvil tip and/or replacement cartridge.

As shown in FIG. 19, loading cartridge (900) comprises a housing (902), a removal side (904), and an installation side (906). Positioned within installation side (906), is anvil tip (919). In the present example, anvil tip (919) comprises a body portion (908) and a shim (910). In some versions, anvil tip (919) is configured for installation within an anvil as shown and described in U.S. patent application Ser. No. 15/435,607 entitled "Surgical Stapler with Insertable Distal Anvil Tip," filed on Feb. 17, 2017, issued as U.S. Pat. No. 10,729,434 on Aug. 4, 2020, and the disclosure of which is incorporated by reference herein. Various other anvil tip configurations suitable for use with cartridge (900) will be apparent to those of ordinary skill in the art in view of the teachings herein. For instance, other anvil tips that may be used with loading cartridge (900) or another similar cartridge include anvil tips (319, 419, 519, 619, 719).

Also positioned within installation side (906), is cartridge (937) that is configured to hold one or more staples. Cartridge (937) may be the same or similar to any of those staple cartridges described herein. For instance, other cartridges that may be used with loading cartridge (900) include cartridges (337, 437, 537, 637, 737, 837). Various other staple cartridge configurations suitable for use with loading cartridge (900) will be apparent to those of ordinary skill in the art in view of the teachings herein.

As shown in FIG. 19, loading cartridge (900) comprises a top side (911) and a bottom side (914). On the installation side (906), anvil tip (919) is selectively retained within top side (911), while cartridge (937) is selectively retained within bottom side (914). For instance, shim (910) is selectively retained within a clamp member (915). Shim (910) further extends partially within body portion (908) of anvil tip (919) to selectively retain body portion (908) within top side (911) of installation side (906) of loading cartridge (900). As shown best in FIGS. 20-22, loading cartridge (900) comprises a clamp member (917) along bottom side (914) that is configured to selectively engage with a distal end of cartridge (937) to selectively retain cartridge (937) within bottom side (914) of installation side (906) of loading cartridge (900). In some other examples, proximal portions of loading cartridge (900) may be configured as engaging portions that selectively engage with the vertical slot (949) of staple cartridge (937) to promote further selective retention of cartridge (937) within loading cartridge (900). In view of the teachings herein, other ways to configure installation side (906) of loading cartridge (900) to provide selective retention of anvil tip (919) and cartridge (937) will be apparent to those of ordinary skill in the art.

Within installation side (906), are guide members (924). In the present example, guide members (924) are located along top side (911) of installation side (906). Guide members (924) are configured to guide end effector (912) being used with loading cartridge (900). In particular, guide members (924) provide a cam action to guide anvil (918) of end effector (912) into position to receive anvil tip (919). Similarly, guide members (924) also provide a cam action to guide lower jaw (916) of end effector (912) into position to receive staple cartridge (937).

Loading cartridge (900) comprises removal side (904) as mentioned above. Removal side (904), like installation side (906), is divided into two compartments (921, 922). Compartment (921) is located along top side (911) of loading cartridge (900), while compartment (922) is located along a bottom side (914) of cartridge (900). Within top side (911) of removal side (904), or within compartment (921), are resiliently biased hooks (926). Hooks (926) are resiliently biased such that when anvil tip (919), such as a previously installed anvil tip (919), of end effector (912) is inserted within compartment (921) and advanced distally toward a distal end (930) of loading cartridge (900), hooks (926) deflect away from the inserted and advancing anvil tip (919). This deflection of hooks (926) permits continued advancing of anvil tip (919) distally. Top side (911) of removal side (904) is further configured such that when anvil tip (919) is fully positioned within removal side (904), hooks (926) resiliently return to their initial non-deflected, or a less deflected, state such that hooks (926) can engage with body portion (908) of anvil tip (919).

Removal side (904) comprises hook (928) as well. Hook (928) is configured to engage shim (910) of anvil tip (919) being removed. For instance, shim (910) being engaged for removal may be from a previously installed anvil tip (919). Hook (928) is also resiliently biased in the present example. This resilient bias allows for hook (928) to deflect away from anvil tip (919) when anvil (918) is inserted within removal side (906). Also, hook (928) comprises a chamfer (932) that is configured to promote deflection of hook (928) when contacted from a proximal side and a force is applied distally. Furthermore, anvil tip (919) is configured such that body portion (908) comprises a space (not shown) beneath shim (910) when anvil tip (919) is fully installed on anvil (918) and shim (910) is fully posited within body portion (908). This space allows for hook (928) to contact shim (910), and when deflected downwardly to slide past shim (910).

Once hook (928) has slid past a head portion of shim (910) and reached a tail portion of shim (910), hook (928) resiliently returns to its initial non-deflected, or a less deflected, state such that hook (928) can engage with the head portion of shim (910). Note that in some other versions, the space for receiving hook (928) may be located within a distal end of shim (910) itself, rather than within body portion (908). In either case, with the engagement of hooks (926) and hook (928) with anvil body portion (908) and shim (910) respectively, end effector (912) can be retracted from removal side (904) and hook (928) will hold shim (910) stationary such that shim (910) is pulled free from a longitudinal slot (not shown) of anvil body (920). Similarly, hooks (926) will hold anvil body portion (908) stationary relative to retracting end effector (912). Consequently, the retention of shim (910) and anvil body portion (908) during retraction of end effector (912) from removal side (904) causes removal of anvil tip (919) from anvil body (920) of anvil (918) of end effector (912). In view of the teachings herein, other ways to selectively disengage an anvil tip from an anvil body of an end effector using loading cartridge (900) or a similar device, will be apparent to those of ordinary skill in the art.

Removal side (904) also includes compartment (922) along bottom side (914). Compartment (922) provides for a space within which a previously installed staple cartridge (937) is removable. In one version, a distal end of bottom side (914) of removal side (904) comprises a resilient clamp member (not shown), similar to clamp member (917) mentioned above. The resilient clamp member on removal side (904) is configurable such that it engages with a distal end of cartridge (937) when end effector (912) is fully advanced within removal side (904). With the clamp member engaged with the distal end of staple cartridge (937), end effector (912) can be opened such that lower jaw (916) moves downwardly and away from loading cartridge (900). With staple cartridge (937) held in place through its engagement with the clamp member of removal side (904) of loading cartridge (900), lower jaw (916) separates from cartridge (937) such that cartridge (937) is removed from lower jaw (916) of end effector (912). In view of the teachings herein, other ways to selectively disengage a staple cartridge from a lower jaw of an end effector using loading cartridge (900) or a similar device, will be apparent to those of ordinary skill in the art. It should also be understood that loading cartridge (900) may include features operable to remove and/or secure anvil tips (910) from/to anvil body (920). Examples of such features are described in U.S. patent application Ser. No. 15/435,607, entitled "Surgical Stapler with Insertable Distal Anvil Tip," filed on Feb. 17, 2017, issued as U.S. Pat. No. 10,729,434 on Aug. 4, 2020, the disclosure of which is incorporated by reference herein.

Similar to installation side (906), within removal side (904) are guide members (934). In the present example, guide members (934) are located along top side (911) of removal side (904). Guide members (934) are configured to guide end effector (912) being used with loading cartridge (900). In particular, guide members (934) provide a camming action to guide anvil (918) of end effector (912) into position to remove anvil tip (919). Similarly, guide members (934) also provide a camming action to guide lower jaw (916) of end effector (912) into position to remove staple cartridge (937).

Figure 21:
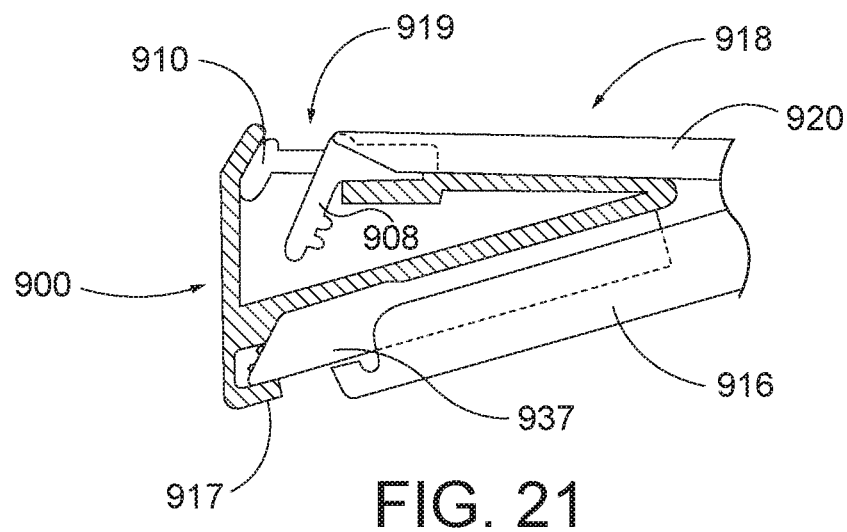
FIG. 21 depicts a second side elevational view in a series of views showing installation of a new anvil tip and cartridge using the tip replacement cartridge of FIG. 19.
Figure 22:
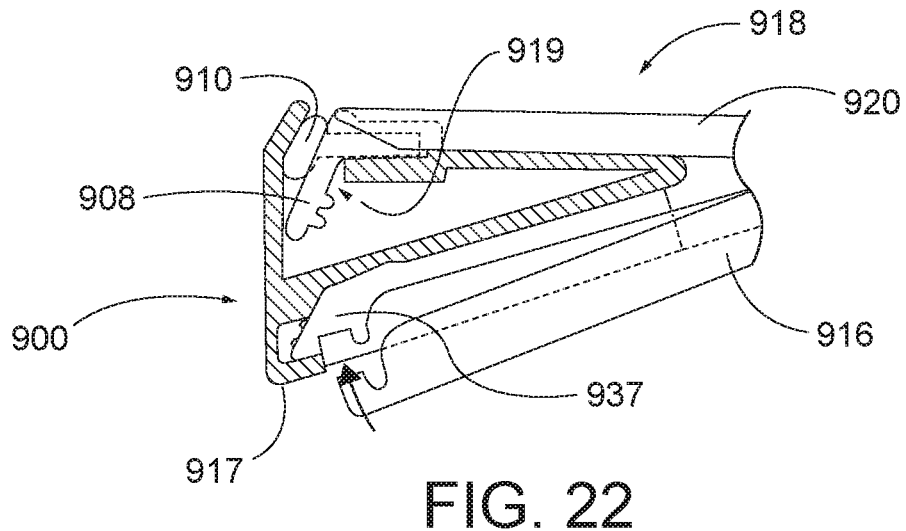
FIG. 22 depicts a third side elevational view in a series of views showing installation of a new anvil tip and cartridge using the tip replacement cartridge of FIG. 19.

FIGS. 20-22 illustrate an exemplary series view showing use of loading cartridge (900) to install anvil tip (919) and staple cartridge (937) with end effector (912). As shown in FIG. 20, end effector (912) is opened to some extent and anvil (918) is aligned and slid within installation side (906). As discussed above, guide members (924) assist in the alignment of anvil (918) when inserting or sliding anvil (918) within top side (911) of installation side (906). As shown in FIG. 20, lower jaw (916) is initially empty such that it can receive cartridge (937).

Referring to FIG. 21, after end effector (312) is aligned with anvil (918) within top side (911) of installation side (906), and lower jaw (916) within bottom side (914) of installation side (906), end effector (912) is advanced distally and closed slightly. In this manner, anvil (918) is moved distally to position an insert portion of anvil body portion (908) within the longitudinal slot of anvil body (920). At or about the same time, lower jaw (916) moves distally and closes to some extent such that cartridge (937) partially resides within lower jaw (916) as shown in FIG. 21.

Referring to FIG. 22, end effector (912) is then advanced further distally relative to loading cartridge (900) such that shim (910) is inserted through anvil body portion (908) and into the longitudinal slot of anvil body (920). With this arrangement, anvil tip (919) is now securely connected with anvil body (920). At or about the same time, lower jaw (916) moves distally and closes further such lower jaw (916) engages cartridge (937) such that cartridge (937) is now securely connected with lower jaw (916). At this point, end effector (912) is retracted from loading cartridge (900) and ready for use. In view of the teachings herein, other ways to modify loading cartridge (900) for use with any of the end effectors described herein, will be apparent to those of ordinary skill in the art. Similarly, in view of the teachings herein, other ways to use loading cartridge (900) or a modified loading cartridge (900) with the end effectors described herein to remove or install anvil tips and/or staple cartridges will be apparent to those of ordinary skill in the art.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body portion; (b) a shaft extending distally from the body portion, wherein the shaft defines a longitudinal axis; and (c) an end effector in communication with the shaft, wherein the end effector is movable between an open configuration and a closed configuration, wherein the end effector is operable to compress, staple, and cut tissue, and wherein the end effector comprises: (i) a cartridge configured to hold one or more staples, wherein the cartridge comprises an angled nose portion, wherein the angled nose portion comprises one or more first features protruding from the nose portion, wherein the one or more first features are configured to contact tissue, (ii) an anvil body, and (iii) an anvil tip configured to be selectively secured with a distal end of the anvil body, wherein the anvil tip comprises a curved portion, wherein the curved portion comprises one or more second features configured to contact tissue, wherein the one or more first features of the cartridge are configured to complement the one or more second features of the anvil tip.

Example 2

The apparatus of Example 1, wherein at least a portion of the anvil tip is elastically deformable and configured to deflect in response to a clamping force applied to the anvil tip.

Example 3

The apparatus of any one or more of Examples 1 through 2, wherein the one or more first features of the cartridge and the one or more second features of the anvil tip are configured to form a nesting arrangement when the end effector is in a closed position without tissue present within the end effector.

Example 4

The apparatus of any one or more of Examples 1 through 3, wherein the one or more second features of the anvil tip are elastically deformable.

Example 5

The apparatus of Example 4, wherein the one or more first features of the cartridge are rigid.

Example 6

The apparatus of any one or more of Examples 1 through 5, wherein a distal end of the cartridge extends further distally than a distal end of the anvil tip.

Example 7

The apparatus of any one or more of Examples 1 through 6, wherein the anvil tip is configured to contact the cartridge when the end effector is in a closed configuration without tissue present within the end effector.

Example 8

The apparatus of any one or more of Examples 1 through 7, wherein the end effector is configured to provide a gap along the anvil tip and the cartridge when the end effector is in a closed configuration without tissue present within the end effector, such that the anvil tip maintains a non-contacting orientation with respect to the cartridge.

Example 9

The apparatus of any one or more of Examples 1 through 8, wherein a select distal-most one of the one or more second features of the anvil tip are positioned distal to the one or more first features of the cartridge.

Example 10

The apparatus of Example 9, wherein a select proximal-most one of the one or more first features of the cartridge are positioned proximal to the one or more second features of the anvil tip.

Example 11

The apparatus of any one or more of Examples 1 through 10, wherein a select distal-most one of the one or more first features of the cartridge are positioned distal to the one or more second features of the anvil tip.

Example 12

The apparatus of Example 11, wherein a select proximal-most one of the one or more first features of the cartridge are positioned proximal to the one or more second features of the anvil tip.

Example 13

The apparatus of any one or more of Examples 1 through 12, wherein the one or more second features of the anvil tip comprise a circular depression in a surface of the anvil tip, and wherein the one or more first features of the cartridge comprise a dome shaped protrusion.

Example 14

The apparatus of Example 13, wherein the anvil tip extends distal to the nose of the cartridge.

Example 15

The apparatus of any one or more of Examples 1 through 14, wherein the anvil body comprises a slot, wherein the apparatus further comprises a shim configured to connect the anvil tip with the anvil body, wherein the shim is selectively insertable within the slot of the anvil body.

Example 16

The apparatus of any one or more of Examples 1 through 15, wherein the one or more second features of the anvil tip comprise a single rib located at a distal end of the anvil tip.

Example 17

An apparatus, comprising: (a) a body portion; (b) a shaft extending distally from the body portion, wherein the shaft defines a longitudinal axis; and (c) an end effector in communication with the shaft, wherein the end effector is movable between an open configuration and a closed configuration, wherein the end effector is operable to compress, staple, and cut tissue, and wherein the end effector comprises: (i) a lower jaw configured to receive and selectively retain a first cartridge configured to hold one or more staples, wherein the first cartridge comprises an angled nose portion, wherein the angled nose portion comprises one or more first features protruding from the nose portion, wherein the one or more first features are configured to contact tissue, (ii) an anvil body configured to receive and selectively retain an anvil tip, wherein the anvil tip comprises a curved portion, wherein the curved portion comprises one or more second features configured to contact tissue, wherein the one or more first features of the first cartridge are configured to complement the one or more second features of the anvil tip, and (iii) a second cartridge configured to selectively connect with the end effector to install the anvil tip to the anvil body, wherein the second cartridge is further to install the first cartridge to the lower jaw.

Example 18

The apparatus of Example 17, wherein the second cartridge is further configured to remove the anvil tip and the first cartridge from the end effector, wherein the second cartridge is further configured to install a replacement anvil tip and a replacement first cartridge.

Example 19

The apparatus of Example 18, wherein the second cartridge comprises a compartment configured to receive the anvil tip, wherein the second cartridge further comprises one or more hook members configured to engage with the anvil tip to retain the anvil tip within the compartment as the end effector is separated from the second cartridge, thereby removing the anvil tip from the end effector.

Example 20

A method of configuring a surgical instrument for use, wherein the surgical instrument comprises: (i) a body portion, (ii) a shaft extending distally from the body portion, and (iii) an end effector in communication with the shaft, wherein the end effector is operable to compress, staple, and cut tissue, wherein the end effector comprises an anvil body configured to receive an anvil tip, and wherein the end effector comprises a lower jaw configured to receive a first cartridge that is configured to hold one or more staples; wherein the method steps comprise: (a) aligning the end effector with a second cartridge, wherein the second cartridge selectively retains the anvil tip and the first cartridge, wherein first cartridge comprises a nose portion having one or more first features, wherein the anvil tip comprises a curved portion having one or more second features, wherein the one or more first features of the first cartridge are configured to complement the one or more second features of the anvil tip; (b) inserting an anvil body of the end effector into an upper compartment of the second cartridge; (c) inserting the lower jaw into a lower compartment of the second cartridge substantially simultaneous with insertion of the anvil body of the end effector into the upper compartment of the second cartridge; (d) advancing the end effector toward the second cartridge to engage the anvil body with the anvil tip; (e) closing the lower jaw of the end effector to engage the lower jaw with the first cartridge; and (f) withdrawing the end effector from the second cartridge.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. patent application Ser. No. 29/594,332, entitled "Surgical Stapler End Effector with Varying Deck Height and Tissue Gripping Features," filed on Feb. 17, 2017, issued as U.S. Pat. No. D836,198 on Dec. 18, 2018, the disclosure of which is incorporated by reference herein. Various suitable ways in which the teachings herein may be combined with the teachings of U.S. patent application Ser. No. 29/594,332, filed on Feb. 17, 2017, issued as U.S. Pat. No. D836,198 on Dec. 18, 2018, will be apparent to those of ordinary skill in the art.

It should also be understood that the teachings herein may be readily combined with various teachings in U.S. patent application Ser. No. 29/594,335, entitled "Circular Surgical Stapler End Effector with Varying Deck Height and Tissue Gripping Features," filed on Feb. 17, 2017, issued as U.S. Pat. No. D833,010 on Nov. 6, 2018, the disclosure of which is incorporated by reference herein. Various suitable ways in which the teachings herein may be combined with the teachings of U.S. patent application Ser. No. 29/594,335, filed on Feb. 17, 2017, issued as U.S. Pat. No. D833,010 on Nov. 6, 2018, will be apparent to those of ordinary skill in the art.

It should also be understood that the teachings herein may be readily combined with various teachings in U.S. patent application Ser. No. 15/435,573, entitled "Surgical Stapler with Elastically Deformable Tip," filed on Feb. 17, 2017, published as U.S. Pub. No. 2018/0235609 on Aug. 23, 2018, the disclosure of which is incorporated by reference herein. Various suitable ways in which the teachings herein may be combined with the teachings of U.S. patent application Ser. No. 15/435,573, filed on Feb. 17, 2017, published as U.S. Pub. No. 2018/0235609 on Aug. 23, 2018, will be apparent to those of ordinary skill in the art.

It should also be understood that the teachings herein may be readily combined with various teachings in U.S. patent application Ser. No. 15/435,607, entitled "Surgical Stapler with Insertable Distal Anvil Tip," filed on Feb. 17, 2017, issued as U.S. Pat. No. 10,729,434 on Aug. 4, 2020, the disclosure of which is incorporated by reference herein. Various suitable ways in which the teachings herein may be combined with the teachings of U.S. patent application Ser. No. 15/435,607, filed on Feb. 17, 2020, issued as U.S. Pat. No. 10,729,434 on Aug. 4, 2020, will be apparent to those of ordinary skill in the art.

It should also be understood that the teachings herein may be readily combined with various teachings in U.S. patent application Ser. No. 29/594,340, entitled "Surgical Stapler with Bent Anvil Tip and Angled Staple Cartridge Tip," filed on Feb. 17, 2017, issued as U.S. Pat. No. D836,199 on Dec. 18, 2018, the disclosure of which is incorporated by reference herein. Various suitable ways in which the teachings herein may be combined with the teachings of U.S. patent application Ser. No. 29/594,340, filed on Feb. 17, 2017, issued as U.S. Pat. No. D836,199 on Dec. 18, 2018, will be apparent to those of ordinary skill in the art.

It should also be understood that the teachings herein may be readily combined with various teachings in U.S. patent application Ser. No. 15/435,631, entitled "Surgical Stapler with Bent Anvil Tip, Angled Staple Cartridge Tip, and Tissue Gripping Features," filed on Feb. 17, 2017, issued as U.S. Pat. No. 10,758,231 on Sep. 1, 2020, the disclosure of which is incorporated by reference herein. Various suitable ways in which the teachings herein may be combined with the teachings of U.S. patent application Ser. No. 15/435,631, filed on Feb. 17, 2017, issued as U.S. Pat. No. 10,758,231 on Sep. 1, 2020, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein: U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body portion;
   (b) a shaft extending distally from the body portion, wherein the shaft defines a longitudinal axis; and
   (c) an end effector in communication with the shaft, wherein the end effector is movable between an open configuration and a closed configuration, wherein the end effector is operable to compress, staple, and cut tissue, and wherein the end effector comprises:
      (i) a cartridge configured to hold one or more staples, wherein the cartridge comprises an angled nose portion, wherein the angled nose portion comprises one or more first features protruding from the angled nose portion, wherein the one or more first features are configured to contact tissue,
      (ii) an anvil body having a longitudinal slot extending from a proximal end of the anvil body distally along the longitudinal axis to a distal end of the anvil body,
      (iii) a cutting member slidably disposed within the longitudinal slot,
      (iv) an anvil tip having a proximal portion configured to be received and selectively retained within a distal end of the longitudinal slot of the anvil body, wherein the anvil tip comprises a curved portion, wherein the curved portion comprises one or more second features configured to contact tissue, wherein the one or more first features of the cartridge are configured to complement the one or more second features of the anvil tip, and (v) a fastener configured to connect the anvil tip with the anvil body, wherein the fastener is insertable through the anvil tip and into the longitudinal slot of the anvil body such that the fastener extends along the longitudinal axis.

2. The apparatus of claim 1, wherein at least a portion of the anvil tip is elastically deformable and configured to deflect in response to a clamping force applied to the anvil tip.

3. The apparatus of claim 1, wherein the one or more first features of the cartridge and the one or more second features of the anvil tip are configured to form a nesting arrangement when the end effector is in a closed position without tissue present within the end effector.

4. The apparatus of claim 1, wherein the one or more second features of the anvil tip are elastically deformable.

5. The apparatus of claim 4, wherein the one or more first features of the cartridge are rigid.

6. The apparatus of claim 1, wherein a distal end of the cartridge extends further distally than a distal end of the anvil tip.

7. The apparatus of claim 1, wherein the anvil tip is configured to contact the cartridge when the end effector is in a closed configuration without tissue present within the end effector.

8. The apparatus of claim 1, wherein the end effector is configured to provide a gap along the anvil tip and the cartridge when the end effector is in a closed configuration without tissue present within the end effector, such that the anvil tip maintains a non-contacting orientation with respect to the cartridge.

9. The apparatus of claim 1, wherein a select distal-most one of the one or more second features of the anvil tip is positioned distal to the one or more first features of the cartridge.

10. The apparatus of claim 9, wherein a select proximal-most one of the one or more first features of the cartridge is positioned proximal to the one or more second features of the anvil tip.

11. The apparatus of claim 1, wherein a select distal-most one of the one or more first features of the cartridge is positioned distal to the one or more second features of the anvil tip.

12. The apparatus of claim 11, wherein a select proximal-most one of the one or more first features of the cartridge is positioned proximal to the one or more second features of the anvil tip.

13. The apparatus of claim 1, wherein the one or more second features of the anvil tip comprise a circular depression in a surface of the anvil tip, and wherein the one or more first features of the cartridge comprise a dome shaped protrusion.

14. The apparatus of claim 13, wherein the anvil tip extends distal to the angled nose portion of the cartridge.

15. The apparatus of claim 1, wherein the fastener includes a shim configured to be inserted proximally into a distal portion of the anvil tip and further into the longitudinal slot of the anvil body.

16. An apparatus, comprising:
(a) a body portion;
(b) a shaft extending distally from the body portion, wherein the shaft defines a longitudinal axis; and
(c) an end effector in communication with the shaft, wherein the end effector is movable between an open configuration and a closed configuration, wherein the end effector is operable to compress, staple, and cut tissue, and wherein the end effector comprises:
(i) a lower jaw,
(ii) a first cartridge configured to be received by the lower jaw and hold one or more staples, wherein the first cartridge comprises an angled nose portion, wherein the angled nose portion comprises one or more first features protruding from the nose portion, wherein the one or more first features are configured to contact tissue,
(iii) an anvil body,
(iv) an anvil tip extending distally from a distal end of the anvil body such that the anvil tip overlies the angled nose portion of the first cartridge, wherein the anvil tip is configured to be received and selectively retained by the anvil body, wherein the anvil tip comprises a curved distal portion that extends angularly towards the angled nose portion of the first cartridge, wherein the curved distal portion comprises one or more second features configured to mate with the one or more first features of the first cartridge, and
(v) a second cartridge configured to selectively connect with the end effector to install the anvil tip to the anvil body, wherein the second cartridge is further configured to install the first cartridge to the lower jaw.

17. The apparatus of claim 16, wherein the second cartridge is further configured to remove the anvil tip and the first cartridge from the end effector, wherein the second cartridge is further configured to install a replacement anvil tip and a replacement first cartridge.

18. The apparatus of claim 17, wherein the second cartridge comprises a compartment configured to receive the anvil tip, wherein the second cartridge further comprises one or more hook members configured to engage with the anvil tip to retain the anvil tip within the compartment as the end effector is separated from the second cartridge, thereby removing the anvil tip from the end effector.

19. An apparatus, comprising:
(a) a body portion;
(b) a shaft extending distally from the body portion, wherein the shaft defines a longitudinal axis; and
(c) an end effector in communication with the shaft, wherein the end effector is movable between an open configuration and a closed configuration, wherein the end effector is operable to compress, staple, and cut tissue, and wherein the end effector comprises:
(i) a cartridge configured to hold one or more staples, wherein the cartridge comprises an angled nose portion, wherein the angled nose portion includes an angled distal face having one or more first protrusions disposed thereon,
(ii) an anvil body having a longitudinal slot extending from a proximal end of the anvil body distally along the longitudinal axis to a distal end of the anvil body, and
(iii) an anvil tip configured to be selectively secured with a distal end of the anvil body, wherein the anvil tip comprises a curved portion that extends toward the angled nose portion, wherein the curved portion includes an angled proximal face having one or more second protrusions disposed thereon, wherein the second protrusions are configured to align longitudinally with the first protrusions when the end effector is in the closed configuration; and (iv) a fastener configured to connect the anvil tip with the anvil body, wherein the fastener is insertable through the anvil tip and into the longitudinal slot of the anvil body such that the fastener extends along the longitudinal axis.

20. The apparatus of claim 19, wherein the fastener includes a head portion and a tail portion, wherein the head portion is configured to be engaged by a removal device for removal of the fastener from the anvil tip.

\* \* \* \* \*